US011907986B2

(12) United States Patent
Raynor et al.

(10) Patent No.: US 11,907,986 B2
(45) Date of Patent: *Feb. 20, 2024

(54) COMPUTER-BASED MARKETPLACE FOR INFORMATION

(71) Applicant: Canary Medical Inc., Vancouver (CA)

(72) Inventors: Michael E. Raynor, Mississauga (CA); William L. Hunter, Vancouver (CA)

(73) Assignee: Canary Medical Switzerland AG, Baar (CH)

( * ) Notice: Subject to any disclaimer, the term of this patent is extended or adjusted under 35 U.S.C. 154(b) by 99 days.

This patent is subject to a terminal disclaimer.

(21) Appl. No.: 17/331,489

(22) Filed: May 26, 2021

(65) Prior Publication Data

US 2021/0366012 A1 Nov. 25, 2021

Related U.S. Application Data

(62) Division of application No. 15/445,884, filed on Feb. 28, 2017, now Pat. No. 11,042,916.

(Continued)

(51) Int. Cl.
*G06Q 30/06* (2023.01)
*G06Q 30/0601* (2023.01)
(Continued)

(52) U.S. Cl.
CPC ......... *G06Q 30/0613* (2013.01); *A61B 5/076* (2013.01); *A61B 5/686* (2013.01);
(Continued)

(58) Field of Classification Search
CPC .... G06Q 30/0613; G06Q 30/08; A61B 5/076; A61B 5/686; A61B 5/11; A61B 2562/0219
(Continued)

(56) References Cited

U.S. PATENT DOCUMENTS 5,363,842 A 11/1994 Mishelevich et al.
5,672,954 A 9/1997 Watanabe
(Continued)

FOREIGN PATENT DOCUMENTS

WO WO-9722297 A1 * 6/1997 ............... A61B 5/00
WO 2014100795 A1 6/2014
(Continued)

OTHER PUBLICATIONS

Article, "Telzuit Medical Technologies, Inc. Investment Profile Issued by Beacon Equity Research", published in Business Wire [New York] Jun. 15, 2006; retrieved from Dialog on Jul. 24, 2023 (Year: 2006).*

(Continued)

*Primary Examiner* — Yogesh C Garg

(57) ABSTRACT

At least one database is organized as a plurality of records, wherein each record contains information associated with one individual person, and a portion of the information is customizable into at least one dynamically productizable dataset. When a request for a plurality of productized datasets is received, and when the request defines fields common to each of the plurality of productized information sets, the database is searched to find records that match the defined fields of the request. Information is retrieved from at least some of the found records that match the defined fields, and at least some of the retrieved information is formed into the plurality of productized datasets. The plurality of productized datasets is communicated to a source of the request.

18 Claims, 14 Drawing Sheets

Related U.S. Application Data

(60) Provisional application No. 62/301,575, filed on Feb. 29, 2016.

(51) Int. Cl.
*G06Q 30/08* (2012.01)
*A61B 5/07* (2006.01)
*A61B 5/00* (2006.01)
*A61B 5/11* (2006.01)

(52) U.S. Cl.
CPC ..... *G06Q 30/0601* (2013.01); *G06Q 30/0611* (2013.01); *G06Q 30/08* (2013.01); *A61B 5/11* (2013.01); *A61B 2562/0219* (2013.01)

(58) Field of Classification Search
USPC ....................................................... 705/26.3
See application file for complete search history.

(56) References Cited

U.S. PATENT DOCUMENTS

| | | | |
|---|---|---|---|
| 7,127,300 | B2 | 10/2006 | Mazar et al. |
| 8,180,591 | B2 | 5/2012 | Yuen et al. |
| 8,475,367 | B1 | 7/2013 | Yuen et al. |
| 8,589,292 | B1* | 11/2013 | Huberman .............. G06Q 30/06 705/37 |
| 9,949,692 | B2 | 4/2018 | Hunter |
| 10,499,855 | B2 | 12/2019 | Hunter |
| 2002/0152183 | A1* | 10/2002 | Soares ................... G06Q 40/04 705/37 |
| 2005/0165317 | A1 | 7/2005 | Turner et al. |
| 2005/0192844 | A1 | 9/2005 | Esler et al. |
| 2005/0242666 | A1 | 11/2005 | Huscher et al. |
| 2006/0232408 | A1 | 10/2006 | Nycz et al. |
| 2008/0088436 | A1 | 4/2008 | Reeves et al. |
| 2008/0215609 | A1 | 9/2008 | Cleveland et al. |
| 2008/0290159 | A1* | 11/2008 | Bartley, Sr. ............ G16H 10/65 340/572.1 |
| 2008/0300659 | A1* | 12/2008 | Matos ................. A61N 1/37282 607/60 |
| 2009/0119222 | A1* | 5/2009 | O'Neil ................. G06Q 50/188 705/14.51 |
| 2009/0194104 | A1 | 8/2009 | Van Sickle |
| 2009/0227883 | A1 | 9/2009 | Zhang et al. |
| 2010/0016860 | A1 | 1/2010 | McCardel |
| 2010/0019294 | A1 | 1/2010 | Velichko et al. |
| 2010/0228977 | A1 | 9/2010 | Sievert et al. |
| 2011/0040611 | A1 | 2/2011 | Simmons et al. |
| 2011/0063094 | A1 | 3/2011 | Meiertoberens et al. |
| 2011/0196815 | A1 | 8/2011 | Acker et al. |
| 2012/0185275 | A1 | 7/2012 | Loghmani |
| 2013/0138524 | A1 | 5/2013 | Sharma |
| 2013/0252610 | A1 | 9/2013 | Kim et al. |
| 2013/0317379 | A1 | 11/2013 | Brimer et al. |
| 2014/0085102 | A1 | 3/2014 | Mccormick |
| 2014/0135612 | A1 | 5/2014 | Yuen et al. |
| 2014/0136237 | A1* | 5/2014 | Anderson .............. G16H 10/60 705/3 |
| 2014/0142403 | A1 | 5/2014 | Brumback et al. |
| 2014/0164611 | A1 | 6/2014 | Molettiere et al. |
| 2014/0180019 | A1 | 6/2014 | Martinez et al. |
| 2014/0197946 | A1 | 7/2014 | Park et al. |
| 2014/0256324 | A1 | 9/2014 | Mohanty et al. |
| 2014/0257047 | A1* | 9/2014 | Sillay ..................... H04L 63/10 600/595 |
| 2014/0275852 | A1 | 9/2014 | Hong et al. |
| 2014/0316296 | A1 | 10/2014 | Meng et al. |
| 2014/0328253 | A1 | 11/2014 | Lee et al. |
| 2015/0126889 | A1 | 5/2015 | Frey et al. |
| 2015/0142511 | A1 | 5/2015 | Gkoulalas-Divanis et al. |
| 2015/0182797 | A1 | 7/2015 | Wernow et al. |
| 2015/0335290 | A1 | 11/2015 | Hunter |
| 2016/0019858 | A1* | 1/2016 | Wang ..................... G06F 1/163 345/520 |
| 2016/0029952 | A1 | 2/2016 | Hunter |
| 2016/0038087 | A1 | 2/2016 | Hunter |
| 2016/0192878 | A1 | 7/2016 | Hunter |
| 2016/0310077 | A1 | 10/2016 | Hunter et al. |
| 2016/0340177 | A1 | 11/2016 | Takada |
| 2017/0138986 | A1 | 5/2017 | Kern |
| 2017/0161434 | A1 | 6/2017 | Naudi |
| 2017/0181825 | A1 | 6/2017 | Hunter |
| 2017/0189553 | A1 | 7/2017 | Hunter |
| 2017/0196478 | A1 | 7/2017 | Hunter |
| 2017/0196499 | A1 | 7/2017 | Hunter |
| 2017/0196508 | A1 | 7/2017 | Hunter |
| 2017/0196509 | A1 | 7/2017 | Hunter |
| 2017/0231494 | A1* | 8/2017 | Pekander ............. A61B 5/0022 340/870.07 |
| 2018/0125365 | A1 | 5/2018 | Hunter et al. |
| 2018/0235546 | A1 | 8/2018 | Hunter |

FOREIGN PATENT DOCUMENTS

| | | |
|---|---|---|
| WO | 2014144070 A1 | 9/2014 |
| WO | 2014144107 A1 | 9/2014 |
| WO | 2014209916 A1 | 12/2014 |
| WO | 2015200704 A1 | 12/2015 |
| WO | 2015200707 A1 | 12/2015 |
| WO | 2015200718 A1 | 12/2015 |
| WO | 2015200720 A2 | 12/2015 |
| WO | 2015200722 A2 | 12/2015 |
| WO | 2015200723 A1 | 12/2015 |
| WO | 2016044651 A1 | 3/2016 |

OTHER PUBLICATIONS

Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.
International Search Report and Written Opinion for International Application No. PCT/US2021/038211, dated Sep. 30, 2021, 17 Pages.

* cited by examiner

| Personal Information Seller |
|---|
| A. Record ID: |
| B. Name: |
| C. Address: |
| D. DoB: |
| E. Gender: |
| F. Device 1: |
| G. Device 1 Info: |
| H. Device 2: |
| I. Device 2 Info: |
| J. ... |
| K. ... |
| L. Device N: |
| M. Device N Info: |
| N. |
| O. Personal Habit 1: |
| P. Personal Habit 2: |
| Q. ... |
| R. ... |
| S. Personal Habit N: |
| T. |
| U. Physical Trait 1: |
| V. Physical Trait 2: |
| W. ... |
| X. ... |
| Y. Physical Trait N: |
| Z. |

| Personal Information Buyer |
|---|
|  |
|  |
| C. Location ID: |
| D. Age Range: |
| E. Gender: |
| F. Device 1: |
| G. Device 1 Info: |
| H. Device 2: |
| I. Device 2 Info: |
| J. ... |
| K. ... |
| L. Device N: |
| M. Device N Info: |
| N. |
| O. Personal Habit 1: |
| P. Personal Habit 2: |
| Q. ... |
| R. ... |
| S. Personal Habit N: |
| T. |
| U. Physical Trait 1: |
| V. Physical Trait 2: |
| W. ... |
| X. ... |
| Y. Physical Trait N: |
| Z. |

| |
|---|
| Price D+F+G: |
| Price D+H+I: |
| Price D+E+L+M |
| Price E+N+R |
| |
| |
| |

| |
|---|
| Offer D+F+G: |
| |
| |
| |
| |
| |
| |

*FIG. 7*

COMPUTER-BASED MARKETPLACE FOR INFORMATION

CROSS-REFERENCE TO RELATED APPLICATION

This application is a divisional of U.S. patent application Ser. No. 15/445,884, filed Feb. 28, 2017, which application claims the benefit under 35 U.S.C. § 119(e) of U.S. Provisional Patent Application No. 62/301,575 filed Feb. 29, 2016, which applications are incorporated herein by reference in its entirety for all purposes.

BACKGROUND

Technical Field

The present disclosure relates generally to devices, systems and methods for generating and creating a market for information More particularly, but not exclusively, the present disclosure relates to devices, systems and methods which provide an electronic forum where entities (e.g., individuals, groups, or commercial organizations) can offer information (e.g., personal information, medical information, behavioral information, etc.) for transfer to third parties by sale, license, or other arrangement; and where buyers can solicit, purchase, license, or otherwise obtain permissible access to use information offered by entities (as illustrated above).

Description of the Related Art

There is already a market for some types of personal information. For example, social networks (e.g., Facebook, Twitter, Reddit, Instagram, Snapchat, WhatsApp, Tumblr, and so on), search engines (e.g., Google, Bing, Yahoo!, etc.), credit bureaus, and others, collect different types of information on various entities (typically, not but exclusively, individuals), including (but not limited to) personal information via a variety of mechanisms, and generate revenue from this information in a variety of ways. For example, by analyzing the information that has been collected, social networks and search engines can identify individuals or groups that meet certain criteria and then selling advertising to third parties that which to reach individuals or groups that meet those criteria.

The individuals on whom information is collected, however, tend to realize value from information about themselves primarily through the use of services that are provided, the use of which generates the information that social networks or search engines then use to sell advertising. There is typically no monetary payment to the provider of the information (e.g., individuals) by the provider of the service (e.g., the social network or search engine). To illustrate, users of a search engine do not pay money to the provider of the search engine for the use of the search engine. Rather, the search engine provider makes the search engine available for use without requiring monetary payment, but collects information about the user's search history, and uses this information to draw conclusions about what sorts of online advertising are most likely to elicit a purchase response if presented to the search engine user, and then solicits advertising revenue from the appropriate advertisers. Alternatively, advertisers can enlist a search engine provider for potential customers based on the analysis of the search histories of users of the search engine. The price secured by the search engine provider for direct or indirect use of the personal information collected via the use of the search engine is determined by the search engine provider in direct negotiation with the advertiser. The information provider—in this example, the individual using the search engine—is not consulted, informed consent to use/sell personal information is typically not obtained from the information provider, and the revenue generated by the sale of the information is not shared with the information provider.

In contrast, some markets for information are very tightly controlled. For example, medical information the physicians, hospitals or insurance carriers that generate or collect medical information typically steward this information with great care, often bound by explicit and extensive legal requirements. Thus, although individuals are subject to a wide range of medical procedures (e.g. physician visits, medication administration, surgical procedures, diagnostic testing procedures, medical imagining procedures, etc.), the medical information generated from these procedures is generally available for use by the patient only upon a specific request, and is generally unavailable to others (outside of a treating physician, hospital, or insurance carrier).

As a consequence, the full scope of a person's medical information is not typically aggregated in a single database. Several attempts have been made to create such databases, e.g., Microsoft's HealthVault, Google Heath, and Apple Health. These efforts have met with limited success: the level of participation and the completeness of the information available have both been too low to create any real value for potential users of that information, by the individuals on whom data are held, or, by other third parties.

Other types of medical information are often not collected at all. For example, when a medical device is implanted into an individual (e.g., a total hip or knee replacement, a vascular stent or graft), the performance of such devices is very often observable only through the interrogation or examination of the patient, or expensive and generally static medical imaging technology (e.g., sonograms, X-rays, MRIs).

For the reasons including, but not limited to, those described in paragraphs above, the creation of datasets of containing information (e.g., the patient's history, results of physical exams, diagnostic tests, etc.) that support more effective and efficient innovation in medical devices or medical procedures has historically been time-consuming, difficult and expensive. Specifically, those who might have the information required to create such dataset have typically needed to be identified, contacted, and solicited for the information one at a time. This has limited the scale (i.e., the number of records that can be included in the dataset), scope (i.e., the number of different fields of information included in each record), accuracy, completeness, reliability and timeliness of the information available. This, in turn, has limited the pace and extent of progress users of this information have been able to make in their respective endeavors.

The present disclosure addresses the above-noted limitations in the creation of datasets that contain relevant information (e.g., personal or medical information). In particular, the present disclosure provides for the automated collection of information (including personal or medical information, such as that generated by sensor-enabled, implantable medical devices and information reported by individuals, such as the patient's self-reported symptoms and self-assessment of physical and emotional wellbeing), as well as a computer-based market in which a variety of users and providers of such information can reach mutually acceptable terms for the access and use of that information (e.g., as compiled into datasets) and payment for such access and use.

All of the subject matter discussed in the Background section is not necessarily prior art, and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

Briefly stated, the present invention provides devices, systems and methods for collecting and analyzing information, and in preferred embodiments aggregating the information into a database, from which can be compiled one or more productizable datasets. For example, within one embodiment, personal information can be obtained pertaining to the state or activity of a person or their possessions, including for example, driving records, credit score, search engine history, activity on social networks, purchasing behavior, marital and familial status, travel, internet search history, purchases and so on. Similarly, personal medical information can be obtained from a large number of sources such as physician and hospital visits, diagnostic procedures, medical and surgical procedures, laboratory tests, imaging studies, superficial monitoring devices, implanted medical devices, physiological testing, psychological testing, rehabilitation procedures, genomic information, subjective information (patient reported symptoms and experiences), and health and fitness monitoring, to name but a few.

Whether pertaining to an individual, a group of individuals, the average characteristics of a defined population, or some other unit of analysis, information, including personal information, has many uses to many parties, including, but not limited to, the individuals or groups described by the information, physicians, medical device companies, pharmaceutical companies, insurance companies, healthcare payers, researchers, governments, public health policy makers, consumer products companies or purchasers of advertising of any type, providers of services of many types (including, but not limited to, legal, accounting, rehabilitation, physiotherapy, renovation, travel-related services, automotive companies, and so on), and so on, are but a few of the groups that may be interested in obtaining access to information, including personal information and personal medical information.

For example, when producers of sensor-enabled medical devices, consumer devices, wearable monitoring devices and other devices are able to study datasets of personal medical information that contain accurate, reliable and timely information on patient behavior and medical device functionality, they might be better able to determine which patients are best-suited for their current devices, and what sorts of design improvements would be most beneficial to future patients. Similarly, when researchers or service providers, such as medical practitioners, are able to study datasets that contain accurate, reliable, and timely personal medical information, they may be better able to determine which treatment regimens are best-suited to which people, and to improve these regimens for the benefit of current and future patients.

Furthermore, augmenting personal medical information with personal information can enhance the ability to improve the medical devices or pharmaceutical products themselves, make medical procedures and treatments more effective and safe, enhance patient compliance to prescribed treatment regimens, improve recovery and rehabilitation efforts, and determine the longer term outcomes, including the safety and efficacy of the treatment undertaken.

In general terms, prospective purchasers of personal information, including, but not limited to, personal medical information, can define the type and quantity of information they seek, the price they are willing to pay, and the terms of use (e.g., for how long the information will be used, and for what purpose). The operator of the market provided for in the current disclosure can then interrogate the database to determine if the requested information is available at the price specified and on the terms specified by the prospective purchaser. If the prospective purchaser's conditions can be met, the productizable dataset will be compiled and the sale will be completed. If the prospective purchaser's conditions cannot be met, the operator of the market can assist prospective purchasers to modify the parameters of their request (e.g., the type of information required, the number of records required, the price offered, and the terms given) and give potential sellers of personal information the opportunity to modify their parameters (e.g., the information they will provide, at what price, and on what terms) in order to allow the market operator to compile an appropriate productizable dataset and enable a transaction to take place.

In general, then, the current disclosure provides for: (1) a way for recipients of, e.g., implantable medical devices, to generate potentially valuable personal medical information; (2) a database that holds this personal medical information and other types of personal medical information provided by the patient, whether generated automatically or by input directly by the patient; (3) a way for entities (including, but not limited to, individuals referenced in (1), immediately above) to generate personal information generally, automatically or by manual input, and contribute this personal information to the database; (4) a market that reveals the value of personal medical information and personal information, and, based on that revealed value, creates incentives to providers of information to contribute information of various types to the database and make them available for sale; (5) a system whereby an entity can provide or withhold consent for the use of personal information (such as medical information) by third parties; and (6) the compilation into productizable datasets of information that has been released for such use.

This Brief Summary has been provided to introduce certain concepts in a simplified form that are further described in detail below in the Detailed Description. Unless and except where otherwise expressly stated, this Brief Summary does not identify key or essential features of the claimed subject matter, nor does it limit the scope of the claimed subject matter.

BRIEF DESCRIPTION OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 2B—an illustrative consideration match module; FIG. 2C—an illustrative auction pool evaluation module; and FIG. 2D—an illustrative auction execution module.

FIG. 7 is a representative embodiment of acceptable seller terms and acceptable buyer terms for a personal information transaction;

DETAILED DESCRIPTION OF THE INVENTION

Figure 1:
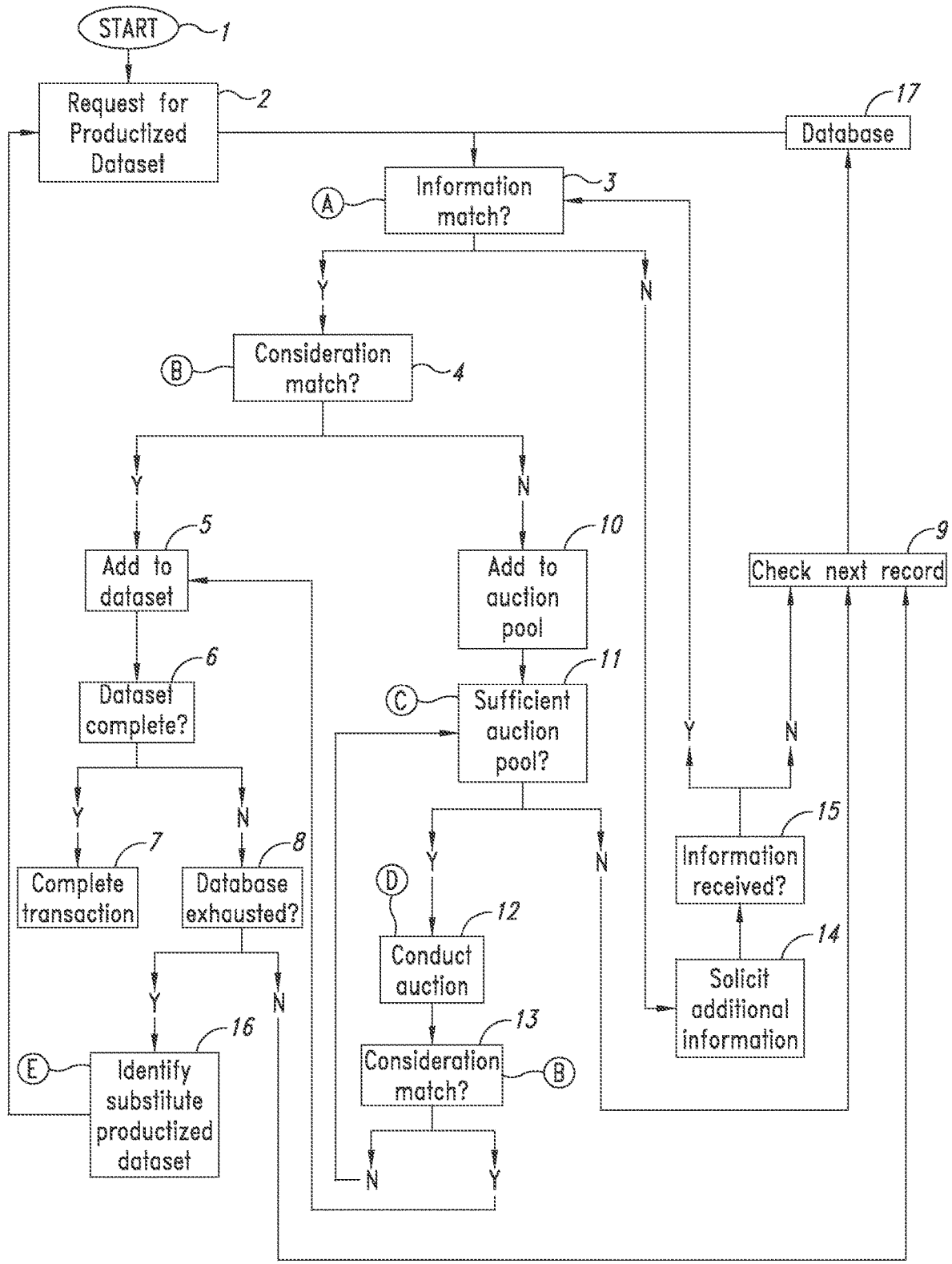
FIG. 1 is a flow diagram illustrating one embodiment of a transaction, in which information contained in the database is compiled into a productizable dataset.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, as well as networks have not been shown or described in detail to avoid unnecessarily obscuring descriptions of the embodiments. Prior to setting forth the embodiments however, it may be helpful to provide an understanding thereof to first set forth definitions of certain terms that are used hereinafter.

"Individual" refers to a single entity (e.g., a living organism such as a human being), where the entity may be further characterized by specific characteristics such as male, female, baby, infant, adolescent, man, woman, person in specific age bracket such as under 18, older than 18, older than 20, older than 25, older than 30, older than 35, older than 40, older than 45, older than 50, older than 55, older than 60, older than 65, older than 70, older than 75, older than 80, older than 85, older than 90, older than 95, and older than 100. The individual may be characterized in terms of health (or by any of a number of different parameters of health), physical characteristics, genetic characteristics, ethnic background, disease state, socioeconomic considerations, geographic considerations, hobbies and activities, habits, drug use, marital status and the like. The individual may be characterized in terms of fitness and mental well-being. The individual may be characterized in terms of typical activities that he or she may perform. "Information" refers generally to facts or knowledge which are gained or learned by any of a variety of mechanisms (e.g., investigation, study, self-reported, etc.). "Information" is also what is conveyed or represented by a particular arrangement or sequence of things, including for example, data.

"Personal information" can be generated through a variety of mechanisms, and includes, for example, information about an individual and that individual's possessions, including driving records and behaviors, credit histories, purchasing behavior, warranty or insurance claims, and any other activities.

In some circumstances, personal information can be captured or produced from a wide variety of sources. Along these lines, personal information may be generated or otherwise derived from browsing information, driving information, purchasing information, location information, social networking information (e.g., FACEBOOK, LINKEDIN, TWITTER, INSTAGRAM, SNAPCHAT, dating sites, etc.), internet of things (IoT) information (e.g., sensor information from automobiles, house climate control systems, home appliances, security systems, home entertainment systems, and other electrical or electromechanical systems), financial transaction information (e.g., PAYPAL, APPLE PAY, GOOGLE PAY, QICSEND, WESTERN UNION, stock market information, etc.), climate information, weather information, travel information (e.g., UBER, airlines, hotels, etc.), media information (e.g., ITUNES, music, news, video, NETFLIX, HULU, VUDU, YOUTUBE, SPOTIFY, PANDORA, APPLE APPS STORE, GOOGLE PLAY, on-line adult content information, etc.), educational information (KHAN ACADEMY, COURSERA, university libraries, etc.), video gaming (e.g., on-line gambling, MINECRAFT, X-BOX LIVE, STEAM, gaming apps, etc.), physical activity (e.g., PELOTON, ZWIFT) and cell phone usage information are other forms of information that are applicable for use in the present invention.

"Personal medical information" refers to information associated with an individual's physiology or psychology, including the individual's physical state, mental state, and emotional state. In the present disclosure, non-limiting examples of personal medical information may include, but is not limited to, physical and electronic medical records information, personal medical imaging information, personal prescription and non-prescription medicament use information, personal surgical and medical procedure information, personal medical testing and diagnostic testing information, personal health and well-being information, personal medical history information, personal psychological and psychiatric information, personal fitness and activity information, personal health monitoring and physical activity monitoring information, personal rehabilitation information, personal genomic information, subjective information (patient reported symptoms and experiences), personal health outcomes information, and personal implanted medical device monitoring information.

Personal medical information may also include information generated by medical practitioners and equipment in hospitals, clinics, and offices during medical procedures, surgical procedures, diagnostic testing procedures, laboratory procedures, medical imagining procedures, genomic testing procedures, rehabilitation procedures, medical and psychological evaluation procedures, physical activity monitoring measures, activity and exercise monitoring measures, physiological monitoring measures, and superficial or internal monitoring device operations. Personal medical information may also include information generated and or self-reported by the person themselves before, during or after treatments; such as pain assessment, duration and quality of sleep, activity levels, functional abilities/disabilities and limitations, quality of life, activities of daily living, psychological and emotional wellbeing, mood, interpersonal assessments, social activities, exercise, and job performance to name a few.

A "productizable dataset" or "productized dataset" consists of a specified number of records capturing specified information (e.g., personal medical information) to which an information buyer is granted a specified use for a specified period of time for specified price. Productizable datasets are not general purpose databases: buyers cannot combine productizable datasets with other information, however obtained, nor can the information in productizable datasets be used to draw inferences that are not explicitly stated in the uses specified when access is granted.

A "buyer" in the present disclosure is an individual or entity that performs acts to gain access to a productized dataset. A buyer may pay or promise to pay money or some other consideration in return for permission to access the productized dataset. Actions to "buy" a productized dataset, as used in the present disclosure, include acts in furtherance of a buyer gaining access to productized dataset. Accordingly, the terms "buy," "buyer," "buying," and derivative and synonymous terms are not limited to a transfer, physical or otherwise, of exclusive ownership in return for consideration. Instead, such terms are broadly interpreted to encompass the acts and means of an individual or entity to acquire exclusive or non-exclusive, perpetual or time-limited access to, and usage subject to specified terms, conditions and limitations of a particular productized dataset.

A "seller" in the present disclosure is an individual or entity that performs acts to include information they own in a productized dataset. A seller may receive money or some other consideration, or a promise thereto, in return for granting permission to include their information in a productized dataset. Actions to "sell" information, as used in the present disclosure, include acts in furtherance of a seller providing access to information that is compiled to create a productized dataset. Accordingly, the terms "sell," "seller," "selling," and derivative and synonymous terms are not limited to a transfer, physical or otherwise, of exclusive ownership in return for consideration. Instead, such terms are broadly interpreted to encompass the acts and means of an individual or entity providing exclusive or non-exclusive, perpetual or time limited access to and usage of, subject to specifiable terms, conditions and limitations, a particular productized dataset "Medical device" refers to an instrument, apparatus, constructed element or composition, machine, implement, or similar or related article that can be utilized to diagnose, prevent, treat or manage a disease or other condition(s). The medical devices provided herein may, depending on the device and the embodiment, be implanted within an individual, utilized to deliver a device to an individual, utilized to deliver a medication or therapy to an individual, utilized to monitor the status, function or physiology of an individual, or, utilized externally on an individual. In many embodiments the medical devices provided herein are sterile, and subject to regulatory requirements relating to their sale and use. Representative examples of medical devices and implants include, for example, cardiovascular devices and implants such as implantable cardioverter defibrillators, pacemakers, balloons, stents, stent grafts, bypass grafts, catheters and heart valves; orthopedic implants (e.g., total or partial arthroplastic joints such as hip, knee and shoulder prosthesis); spinal implants and hardware (spinal cages, screws, plates, pins, rods and artificial discs); a wide variety of medical tubes (grafts, bypass grafts, shunts, drains, endotracheal tubes), cosmetic and/or aesthetic implants (e.g., breast implants, fillers); a wide variety of polymers, bone cements, bone fillers, scaffolds, and naturally occurring materials (e.g., xenograft heart valves, and grafts from other naturally occurring sources); intrauterine devices; infusion devices (pumps, ports, vascular access devices) orthopedic hardware (e.g., casts, braces, tensor bandages, external fixation devices, tensors, slings and supports) and internal hardware (e.g., K-wires, pins, screws, plates, and intramedullary devices (e.g., rods and nails), dynamic hip screws); cochlear implants; dental implants; medical polymers (including sutures, ligatures, meshes, barriers, sealants, glues and gels), a wide variety of neurological devices (stimulation devices); and artificial intraocular eye lenses.

"Sensor" refers to a device that detects and or measures a physical property, and can, optionally, record, indicate and/or respond to the physical property (and include for example, "ISM"s as discussed in more detail below). Sensors can be utilized to detect and/or measure a wide variety of physical properties, including for example, movement, acceleration, velocity, location, pressure, force, biological properties, and time. Within various embodiments of the invention sensors can detect and/or measure body tissue (anatomy, physiology, metabolism, and/or function) and/or one or more aspects of the medical device. Representative examples of sensors suitable for use within the present invention include, for example, fluid pressure sensors, fluid volume sensors, contact sensors, optical sensors, position sensors, pulse pressure sensors, blood volume sensors, blood flow sensors, chemistry sensors (e.g., for blood chemistry and/or other fluids), metabolic sensors (e.g., for blood and/or other fluids), antibodies, accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor and/or a Unique Device Identification number ("UDI") with which the sensors can provide unique information of the associated Medical device for tracking purposes of the Medical Device manufacturer, the health care system, and regulatory requirements.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE-The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations,"*J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 $cm^3$ Interferometric Accelerometer with Nano-g Resolution," *J. Microelectromechanical Sys.*, 11:3, June 2002, 182-187; all of the above of which are incorporated by reference in their entirety.

Within various embodiments of the invention the sensors described herein may be placed at a variety of locations and in a variety of configurations, on or within an object, on or within an individual, on the inside of a medical device, within the body of the medical device, on the outer surfaces (or inner surfaces) of the medical device, between the medical device and other medical devices or implants, and/or between the medical device and any device that might carry or deliver it (e.g., a delivery device, injection device, or surgical instrument). When the phrase "placed in a medical device" or "placed in a medical implant" is utilized, it should be understood to refer to any of the above embodiments (or any combination thereof) unless the context of the usage implies otherwise.

The sensors may be placed on and/or within an object in a wide variety of configurations. For example, within certain embodiments, objects are provided (e.g., wearable items, sports equipment, an area of play, and/or a medical device) which comprise sensors at a density of greater than 1, 2, 3, 4, 5, 6, 7, 8, 9, 10 or greater than 10 sensors per square centimeter. Within other aspects, objects are provided (e.g., wearable items, sports equipment, an area of play, and/or a medical device) which comprise sensors at a density of greater than 1, 2, 3, 4, 5, 6, 7, 8, 9, 10 or greater than 10 sensors per cubic centimeter. Within either of these embodiments, there can be less than 50, 75, 100, or 100 sensors per square centimeter, or per cubic centimeter. Within various embodiments, at least one or more of the sensors may be placed randomly, or at one or more specific locations within an object.

In various embodiments, the sensors may be placed within specific locations and/or randomly throughout the medical device and/or associated devices. In addition, the sensors may be placed in specific patterns (e.g., they may be arranged in the pattern of an X, as oval or concentric rings around the orthopedic implant and/or associated devices).

"Implantable Sensor Module" or "ISM" is a sensing device which is configured to be implanted into, a living individual, such as a human, and is configured to sense one or more physical quantities, to generate a signal that represents the sensed quantity, and to transmit the signal to a remote receiver. The ISM may have one or more sensors as provided above. The ISM may be implanted into an individual directly, or, within one or more medical devices which are implanted within an individual. Within an embodiment, the signal may contain information encoded to represent one or more of a magnitude, phase, and type of the sensed physical quantity.

Within one embodiment of the invention, the ISM is a self-contained module having one or more sensors as described herein, a sensor interface, a processor interface, battery management, a transmitter, and a wireless interface. Within preferred embodiments of the invention the ISM will be less than 5, 4, 3, 2, or 1 cubic centimeter in size, and more preferably, less than 5.0, 4.5, 4.0, 3.5, 3.0, 2.5, 2.0, 1.5, 1.0, 0.9, 0.8. 0.7, 0.6, 0.5, 0.4, 0.3, 0.2, or 0.1 cubic centimeters in size. Within various embodiments the ISM can be comprised of a solid outer core, or composed of flexible materials (e.g., flexible/malleable alloys, a degradable or non-degradable outer polymeric surface). Within related embodiments, the ISM can be comprised of flexible circuitry (including for example, single and double-sided flexible circuits. Within certain embodiments the ISM may be relatively square and solid, and yet with in other embodiments very thin, pliable and lengthy (as compared to its width and/or height). It can be constructed for a number of different applications (e.g., for insertion, attachment or implantation into any of the medical devices or implants provided herein).

Representative examples of various objects (e.g., implantable medical devices, including for example, wireless medical devices which can transmit a signal from inside a body to outside the body) having one or more sensors as provided herein, as well as methods for sending and receiving signals from such objects include those described in the following patent applications (all of which are hereby incorporated by reference in their entirety): U.S. Ser. No. 14/654,529 and International Application No. PCT/US2013/077356, entitled STENT GRAFT MONITORING ASSEMBLY AND METHOD OF USE THEREOF; U.S. Ser. No. 14/776,646 and International Application No. PCT/US2014/028323, entitled STENT MONITORING ASSEMBLY AND METHOD OF USE THEREOF; U.S. Ser. No. 14/776,650 and International Application No. PCT/US2014/028381, entitled DEVICES, SYSTEMS AND METHODS FOR MONITORING HIP REPLACEMENTS; U.S. Ser. No. 14/392,173 and International Application No. PCT/US2014/043736, entitled DEVICES, SYSTEMS AND METHODS FOR MONITORING KNEE REPLACEMENTS; U.S. Ser. No. 15/320,275 and International Application No. PCT/US2015/037823, entitled DEVICES, SYSTEMS AND METHODS FOR USING AND MONITORING TUBES IN BODY PASSAGEWAYS; U.S. Ser. No. 15/320,279 and International Application No. PCT/US2015/037803, entitled DEVICES, SYSTEMS AND METHODS FOR USING AND MONITORING IMPLANTS; U.S. Ser. No. 15/320, 284 and International Application No. PCT/US2015/037825, entitled DEVICES, SYSTEMS AND METHODS FOR USING AND MONITORING SPINAL IMPLANTS; U.S. Ser. No. 15/320,289 and International Application No. PCT/US2015/037827, entitled DEVICES, SYSTEMS AND METHODS FOR USING AND MONITORING ORTHOPEDIC HARDWARE; U.S. Ser. No. 15/320,292 and International Application No. PCT/US2015/0037828, entitled POLYMERS, SYSTEMS AND METHODS FOR USING AND MONITORING POLYMERS FOR USE IN MEDICAL POLYMERS, IMPLANTS, AND PROCEDURES; U.S. Ser. No. 15/320,296 and International Application No. PCT/US2015/037810, entitled DEVICES, SYSTEMS AND METHODS FOR USING AND MONITORING HEART VALVES; U.S. Ser. No. 15/078,604 and International Application No. PCT/US2015/050789, entitled DEVICES, SYSTEMS AND METHODS FOR USING AND MONITORING MEDICAL DEVICES; and U.S. Serial Nos. 62/312, 072, 62/312,079, 62/312,095, 62/312,108, 62/312,114, 62/312,120, 62/312,131, 62/312,180, 62/312,188, 62/312, 193, 62/312,197, and 62/312,205.

Other representative examples of various objects (e.g., wearable items, sports equipment, an area of play, and/or external medical devices) having one or more sensors as provided herein include those described in the following patent applications (all of which are hereby incorporated by reference in their entirety): U.S. Ser. No. 62/220,239 and U.S. Ser. No. 15/268,575 entitled DEVICES, SYSTEMS AND METHODS FOR USING AND MONITORING SPORTS EQUIPMENT AND SPORTS ACTIVITIES, as well as U.S. Pat. Nos. 8,180,591 and 8,475,367, and U.S. Serial Nos. 2014/0275852, 2014/0142403, US2014/0197946, US2014/0180019, US2014/0164611, US2014/0135612 and US2015/0182797. Other examples of external devices include, for example, those described in U.S. Pat. No. 5,363,842, and in U.S. Serial Nos. 2009/0194104, 2010/016860 and 2010/019294, 2013/0317379, 2014/0316296, and 2015/0126889.

The present invention may be understood more readily by reference to the following detailed description of the preferred embodiments of the invention. It is to be understood that the terminology used herein is for the purpose of describing specific embodiments only and is not intended to be limiting. It is further to be understood that unless specifically defined herein, the terminology used herein is to be given its traditional meaning as known in the relevant art. Any headings used within this document are only being utilized to expedite its review by the reader, and should not be construed as limiting the invention or claims in any manner. In order to further understand the various aspects of the invention provided herein, the following sections are provided below: A. A Representative Dataset Transaction; B. A Representative System to Collect Information; C. One Representative Example of an Artificial Joint; and D. General Considerations A. A Representative Dataset Transaction One example of a representative dataset transaction is provided in FIG. 1. In this embodiment, information that is owned by an individual or an entity may be transferred to another individual or entity in exchange for consideration. The consideration can be money, a future promise, access to research or other technical information that results from use of the dataset, particular medical treatment, or some other form of compensation, and includes a specification of the terms governing the use of the information provided.

Processing in this embodiment of an information transaction begins at the START (1). Briefly, a request (2) for a productized dataset is made. The request consists of two elements: a specification of the dataset and a specification of the consideration offered for the information in the dataset. The specifications for the dataset can include a variety of parameters, including for example: (i) information captured in specific fields of records that define the records in a database, at 17, that will be searched. The information in these specified fields can include personal information, including personal medical information, (e.g., demographic information, medical information, patient-reported information, manufacturer information, technological information, or nearly any other kind of information that is relevant to the dataset being requested); (ii) The number of records required to constitute the desired dataset that contain information in each of the specified fields; and (iii) The selection protocol by which records with information in each of the specified fields will be included in the desired dataset.

The specifications of the consideration to be provided for the information can also include a variety of parameters, including for example: (i) The terms of use for the information in the dataset, including, but not limited to, the user, usage and purpose of the collected information (e.g. Company for market research, an academic for basic science research, a device manufacturer for product performance assessment, etc.); and the time period for which the information in the dataset can be used; and (ii) the compensation to be provided to the owners of the information.

For example, if a research study is being undertaken to determine patterns or trends with a particular implantable medical device from a particular manufacturer, a researcher can determine how many individuals have had the subject device implanted in a particular location during a particular time. This number of individuals may be considered a targeted device population ("population"). The researcher can further determine how many cases within the targeted device population they wish to include in a dataset in order to reach meaningful conclusions. This number of individuals may be considered the sample of the device population ("sample"). The researcher can further determine what information is required from each individual in the sample. The researcher can also determine the price they are willing to pay for this information. Based on these determinations, the researcher can provide a request for a Productized Dataset (2).

A particular database is maintained (17). Within the database, a plurality of records is stored. The records are comprised of a plurality of fields, which may also include subfields or some other units of information. Each record, or groups of records, can also include other information such as a pre-set price, which may include either or both of consideration to be paid for granted access to the information and the terms on which such access is granted, that an owner of the information has already agreed to.

Each record in the database can be assigned to a particular individual owner. In many cases, the individual owner is also the individual whose information is represented in the record. For example, when fields in the record store medical information, the individual owner may be the patient whose treatment generated the medical information. In other cases, a particular record has been transferred from its individual owner to another owner who may be an individual or an entity. One individual may own a plurality of records. One entity may own a plurality of records. The owner of the record, or a surrogate for the owner, is empowered to make decisions regarding the inclusion of their information within the record. Specifically, the owner of the record is empowered to determine if their information is used and for what purposes it is being used (informed consent).

An information match module (3), which can be executed using subroutine A (see FIG. 2A), extracts a record from the database (17) and compares the content of the record with the parameters that define the request for the productized dataset (2). In subroutine A, the productized dataset request (2) is used to generate search criteria at 20. At 21, a record is extracted from the database at 17 (see FIG. 1), and at 22 the information contained in the record is compared with the information criteria. If the record meets the information criteria, processing passes to 4 (see FIG. 1) and if not, processing passes to 14 (see FIG. 1).

Figure 2A:
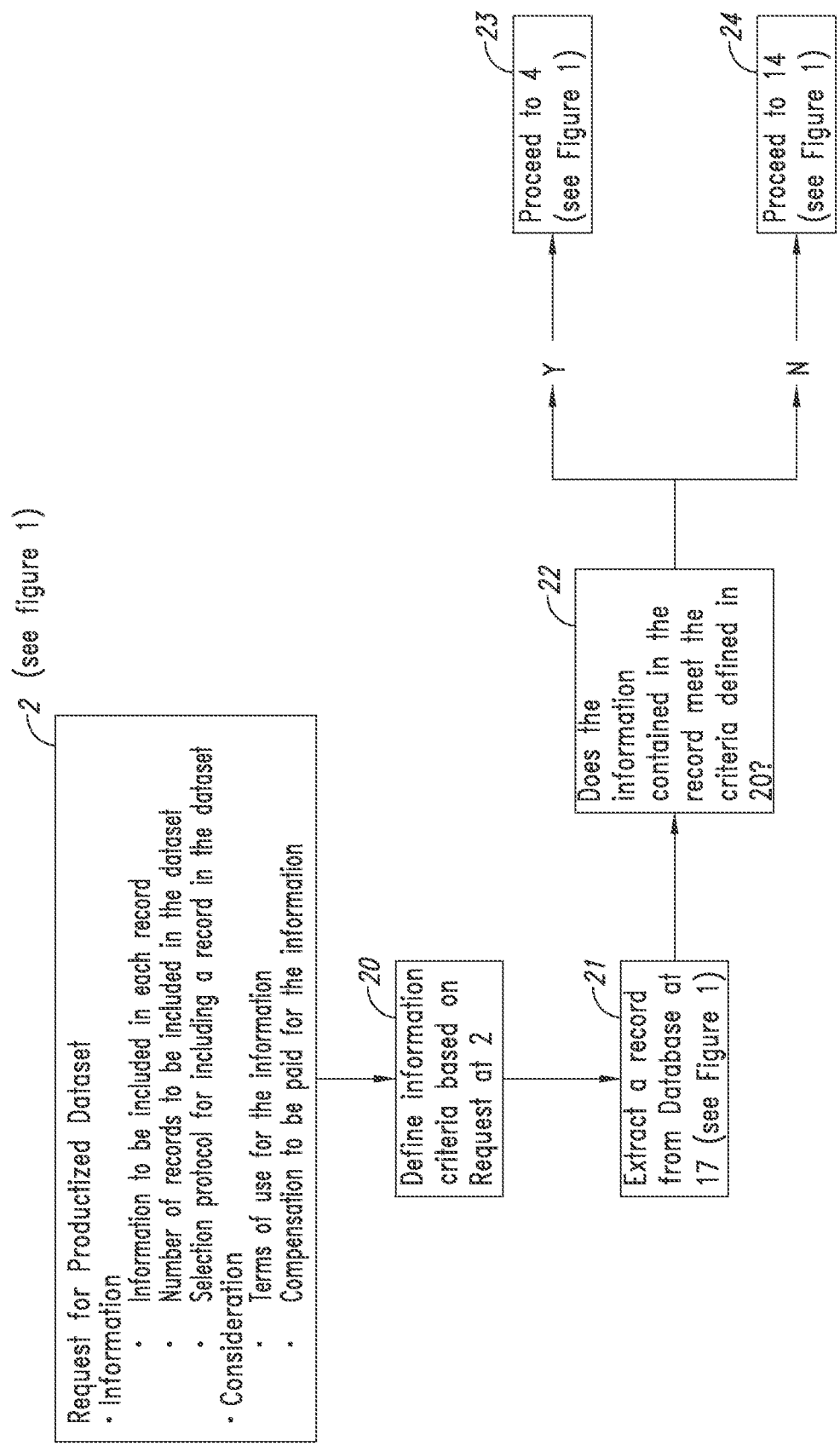
FIGS. 2A, 2B, 2C, and 2D are a series of diagrams illustrating various subroutines, including FIG. 2A—an illustrative information match module.
Figure 2B:
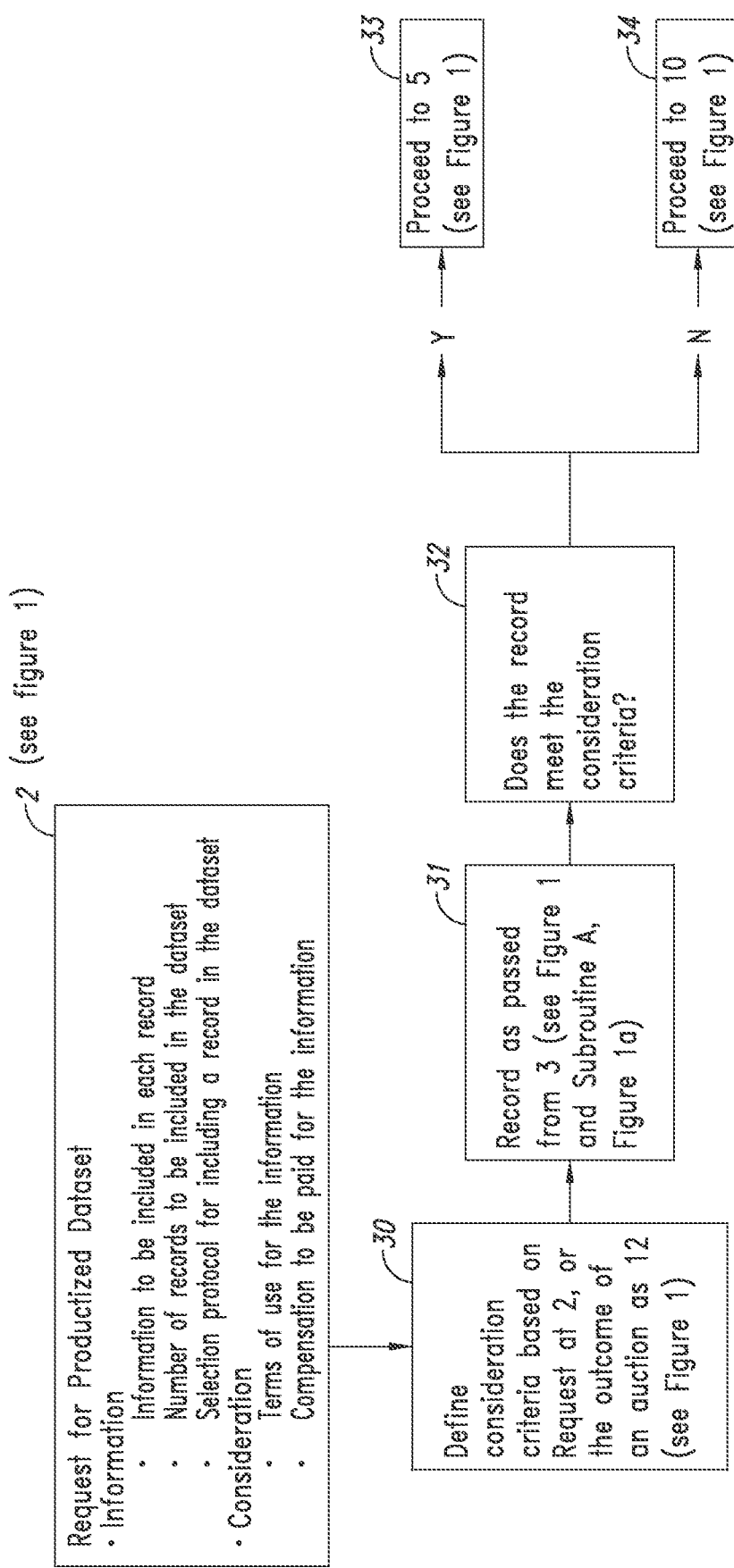

If Subroutine A passes processing from 3 to 4 in FIG. 1, a Consideration Match module is invoked, which can be executed using subroutine B (see FIG. 2B). At 30 compensation criteria are defined using the request for the productized dataset at 2 (see FIG. 1), or using the consideration criteria arising from the outcome of an auction at 12. At 31, the record passed from 3 (see FIG. 1) and subroutine A (see FIG. 2A) is fetched, and at 32, the relevant fields from the record are compared with the compensation criteria from 30. If the relevant fields match the compensation criteria, at 33 processing passes to 5 (see FIG. 1), and if not, at 34 processing passes to 10 (see FIG. 1).

If subroutine B (see FIG. 2B) has passed processing to 5, the record matches both the information and consideration requirements for inclusion in the productized dataset, and so the record is included in the productized dataset. Processing then passes to 6, where the dataset compiled to this point in the process is compared with the requested productized dataset. If the dataset is complete, the transaction is completed at 7. Completing the transaction (7) requires creating the productized dataset, which can include consolidating the records, transferring the productized dataset to the requestor, compensating the information owner(s) or other authorized party or parties, updating records in the database to reflect the transaction, and other tasks. Productizing the dataset, as described herein, will include formatting the information so that it conforms to the agreed-upon terms, which may include removing personally identifiable information (i.e., anonymizing the data), obfuscating (e.g., encrypting) the data for security purposes, preparing and/or implementing a terms-of use agreement corresponding to details of the transaction, forming the information into one or more computer-readable files, and the like. If the dataset is not complete, processing passes to 8.

At 8, it is determined whether or not all the records in the database have been compared with the information and consideration criteria. If unexamined records remain in the database, processing passes to 9, where the next record in the database is fetched from the database at 17, and processing passes back to 3, which invokes subroutine A.

If a record that has been passed from subroutine B to 10 (because it has failed to meet the compensation criteria), that record is added to the "auction pool" at 10. The Auction pool consists of all those records that meet the search criteria defined in subroutine A but do not explicitly meet the compensation criteria in subroutine B. With each addition of a record to the auction pool, processing passes to 11, which invokes subroutine C (see FIG. 2C).

Subroutine C imports the consideration criteria defined at 30 in subroutine B (see FIG. 2B). At 41, an analysis of the records contained in the auction pool, as defined at 10 in FIG. 1, reveals the nature of the known consideration requirements of the owners of the relevant records. At 42, a comparison of the consideration criteria with the consideration requirements of the auction pool considered as a population allows for the determination of an optimal auction algorithm at 43; that is, an auction algorithm that comes closer than any other practical auction algorithm that can be executed within a reasonable time at reasonable cost, to maximizing the likelihood that the request for the productized dataset can be met. At 44, the results of the optimal auction algorithm are modeled using computerized simulations. If the results of these simulations are acceptable, processing passes to 45, which passes processing back to 12 (see FIG. 1). If the results of the simulations are unacceptable, processing passes to 46, which passes processing back to 9 (see FIG. 1).

Figure 2C:
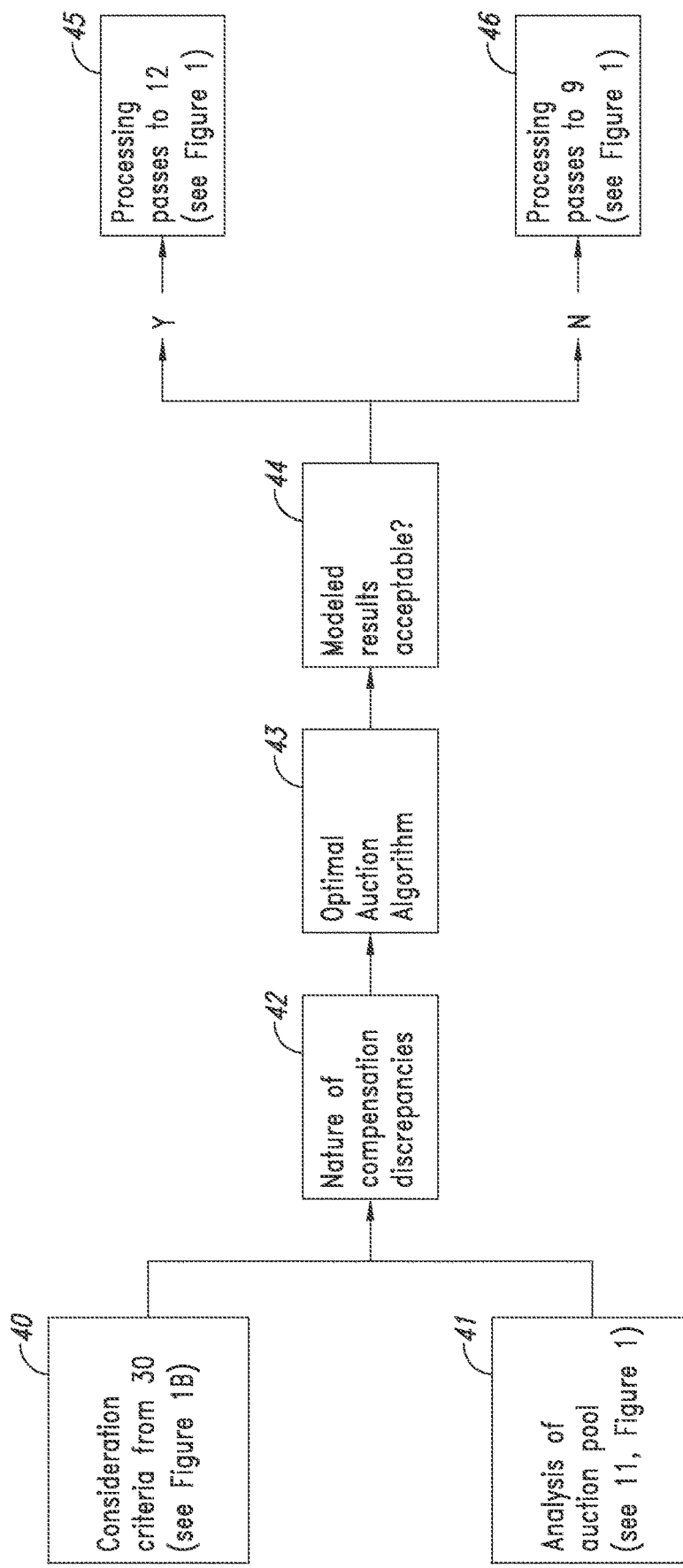
Figure 2D:
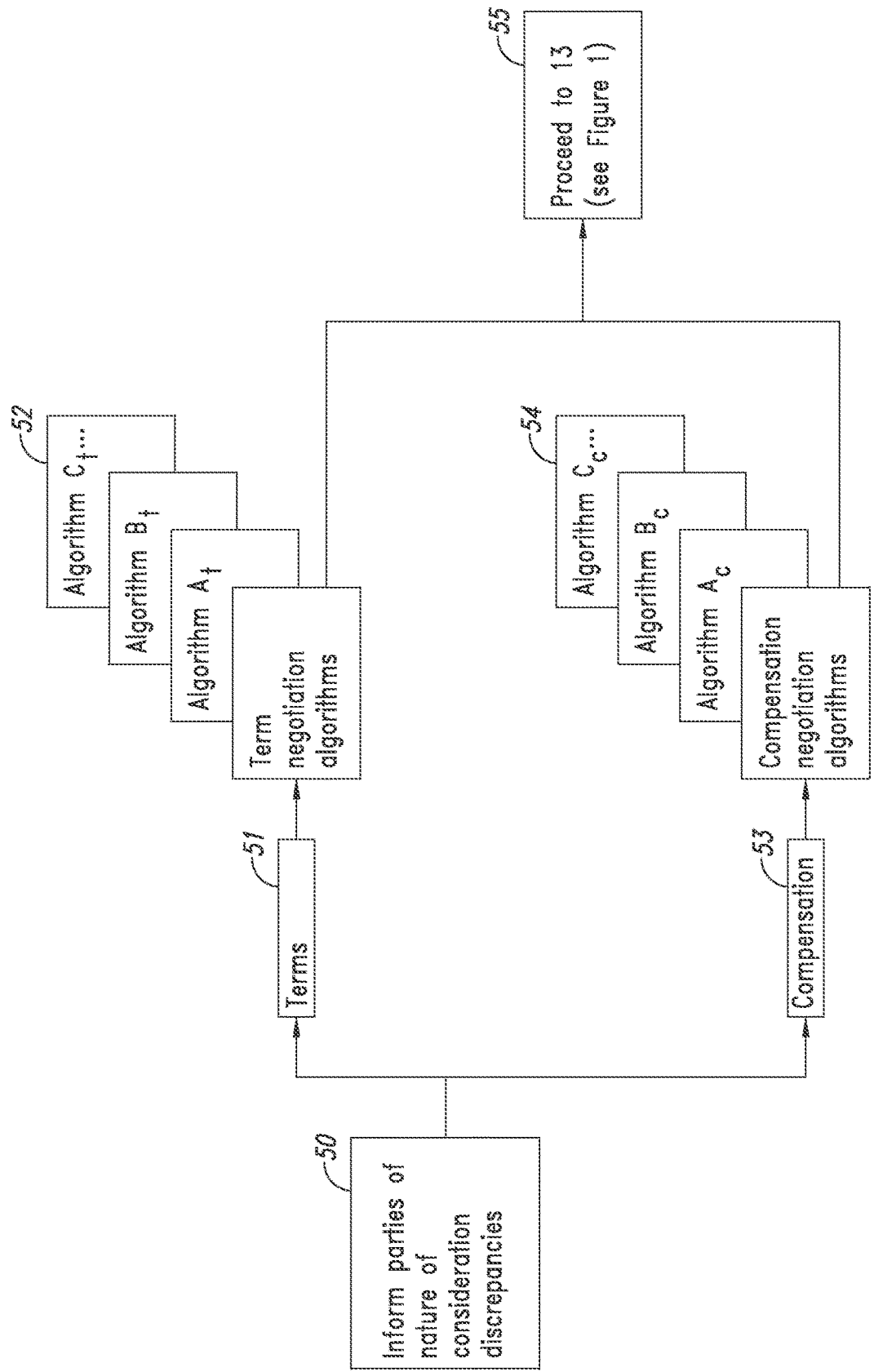

If processing passes from 11 (see FIG. 1) to 12, the auction is conducted using the optimal algorithm identified in subroutine C, by invoking subroutine D (see FIG. 2D). At 50, the owners of the information contained in the records included in the auction pool are informed of the discrepancies between the offered consideration and the consideration required either by themselves individually or by the auction pool as a whole, or of some subset of the auction pool, as dictated by the optimal auction algorithm, as defined in subroutine C. These discrepancies are divided into discrepancies related to terms, at 51, and discrepancies related to compensation, at 53. At 52 and 54 auction algorithms are run which create an opportunity for the requester of the productized dataset and the owners of the information contained in the relevant records to define mutually acceptable consideration for the inclusion of the information in the productized dataset. The outcomes of the overall auction algorithm (whether consisting of multiple algorithms or only one) for each record included in the auction pool are passed, at 55, to 13 (see FIG. 1).

At 13 (see FIG. 1), the outcomes of subroutine D are processed using the consideration match module, which is subroutine B, described above (see FIG. 2B). If a record now meets the consideration criteria, either as originally stated or as revised through auction process, processing passes to 5. Should enough records have been added to the dataset as a result of revising the consideration criteria or revising the information owners' requirements that the dataset is now complete, as assessed at 6, processing passes to 7, and the transaction is completed.

In various embodiments described above, processing was passed to 4 by subroutine A. If, alternatively, subroutine A passes processing from 3 to 14, a record does not contain the information specified in the productized dataset request. At 14, additional information is solicited from the owner of the information contained in the relevant record. This consists of informing the owner of the information contained in the relevant record of (a) what additional information is requested; (b) the consideration offered for the information; (c) the appropriate mechanism for providing the relevant information. If the information is provided, processing passes to 3, and the revised record is processed by subroutine A. If the additional information is not supplied, processing is passed to 9, and the next record is fetched from the database at 17.

In other embodiments described above, processing was passed from 8 to 9 because unexamined records remained in the database. Alternatively, if all the records in the database have been examined and the requested productized dataset remains incomplete, processing passes to 16, which defines an alternative request for a productized database (e.g., through subroutine E). For example, if a buyer is seeking data from a single city, and an insufficient number of records were located, the system may suggest a wider geographic area such as a county that includes the city. As another example, if a buyer is seeking data associated with men between the ages of 25 and 30, and an insufficient number of records were located, the system may suggest a wider age range, or data that includes both men and women. As another example, if an insufficient number of records were located, the system may suggest a smaller number of records. As another example, an alternative, and likely higher, price may be suggested, or more lenient terms of use might be suggested, in order to entice owners of data that refused the initial offer to accept. More generally, different terms and considerations will be suggested that are likelier to result in completing a request for a productized dataset while still addressing the needs that motivated the original request. Pending acceptance, either on the basis of what is suggested by the embodiment or other means, a modified request for a productized dataset is triggered, and processing passes to 2.

Processing ends with a completed transaction (7).

B. A Representative System to Collect Information

Figure 3:
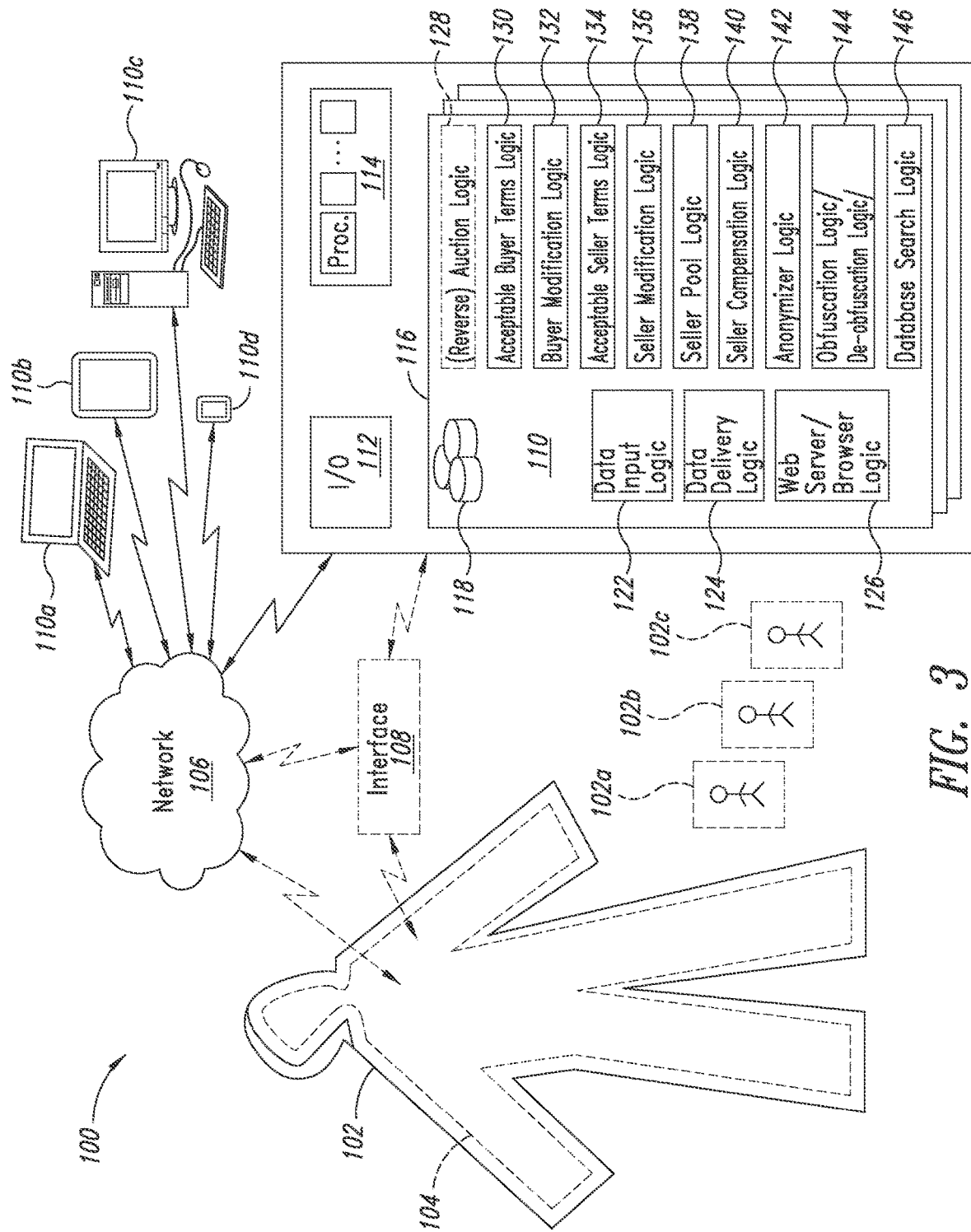
FIG. 3 illustrates one embodiment of a system to collect personal information and provide a computer-based marketplace to license, sell, or otherwise grant access the collected personal information.

FIG. 3 illustrates one representative system 100 to collect personal information and provide a computer-based marketplace to sell the collected personal information. Briefly, an individual 102 has an implanted medical device 104. The implanted medical device 104 may be a mechanical device, an electromechanical device, a chemical delivery device, or some other implanted medical device as provided herein. For example, the implanted medical device 104 may be a pacemaker or another type of electromechanical device, an artificial joint, a stent or a different medical device to support an internal biological structure, an insulin pump or another pump to move a medicament into or through a patient, or some other medical device. Additional examples of medical devices include cardiovascular implants such as implantable cardioverter defibrillators, stent grafts, bypass grafts, catheters, balloons and heart valves, orthopedic replacement prosthesis such as legs and hands, orthopedic implants such as hip, shoulder and knee prosthesis, spinal implants and hardware (spinal cages, screws, plates, pins, rods and artificial discs), intrauterine devices; orthopedic hardware used to repair fractures and soft tissue injuries (casts, braces, tensor bandages, plates, screws, rods, pins and plates), cochlear implants, aesthetic implants (breast implants, fillers), dental implants, medical polymers; and artificial intraocular eye lenses. Within alternative embodiments of the invention the medical device may be external to the body (e.g., a wearable device).

The implanted medical device 104 is configured to deliver data associated with the implanted medical device 104 and particularly associated with the individual 102. The data may be considered personal medical information. In many cases, the data includes technical performance information regarding the implanted medical device 104. The technical performance information may include range of motion or stress regarding an artificial joint, number of cycles for a pacemaker or pump, blood or other bodily fluid volume, pressure, flow or composition data, or other like information. The technical performance information may also include an identification number that can uniquely identify the implanted medical device 104 within a particular group of other implantable medical devices. The technical performance information may include information that ties the implanted medical device 104 to the particular individual 102. The technical performance information may include physiological information associated with the operation of the implanted medical device 104 in the body of the individual 102. The technical performance information may include patient-reported information such as pain, function, activity, quality of life, sleep, medication usage, emotional and psychological wellbeing, and rehabilitation efforts.

In FIG. 3, a first individual 102 is illustrated along with an optional plurality of other individuals 102a-102n. Within the context of this disclosure, an individual 102 is referenced. It is understood, however, that any number of other individuals having any number of same or different types of implantable medical devices are contemplated.

The implantable medical device 104 includes a communication interface that allows data collected and stored in the device to be communicated outside of the body of the individual 102. In some implementations, the implantable medical device 104 communicates directly with an outside network 106. In other cases, the implantable medical device 104 communicates directly with an interface device 108. The implantable medical device 104 may include a first portion that is implanted inside the body of the individual 102, though in other cases, the implantable medical device 104 may also include a second portion that is completely or partially outside of the body of the individual 102. In this way, the data generated or otherwise collected by the implantable medical device 104 may communicate the data in a wired or wireless fashion to the outside world. The communications may be facilitated by a proprietary wired or wireless protocol, a universal serial bus (USB) protocol, a Bluetooth protocol, a single wire interface (SWI) protocol, or some other protocol. Accordingly, the communication may occur in a unidirectional or bidirectional peer-to-peer exchange, personal area network (PAN), local area network (LAN), or wide area network (WAN).

Network 106 may be configured to include some or all portions of personal area networks (PANS), local area networks (LANs), or wide area networks (WANs). For example, communications from the implantable medical device 104 may be via a Bluetooth PAN connection, a Wi-Fi or wired LAN connection, a GSM or CDMA cellular WAN connection, or in some other way.

Interface 108 is shown as an optional device. Interface 108 may be electromechanically coupled to the implantable medical device 104 in cases where the device has a corresponding port accessible from outside of the body of the individual 102. In other cases interface 108 is a portable device placed in proximity of the implantable medical device 104. For example, if the implantable medical device includes a radio frequency identification (RFID) module, then interface 108 may be configured as an RFID terminal host located in the office of a medical practitioner. When the individual 102 visits the office of the medical practitioner, the medical practitioner uses the interface 108 during an examination of the individual 102, and interface 108 collects data from the implantable medical device 104. In yet other cases, interface 108 may include a Bluetooth transceiver configured as a master device capable of interrogating the implantable medical device 104 to collect information. Other configurations and communication technologies are considered.

Marketplace computing server 110 illustrates portions of a non-limiting embodiment of a computing server that includes operative hardware found in a conventional computing device such as one or more processing units 114, volatile and non-volatile memory 116, and serial and parallel input/output (I/O) circuitry 112 compliant with various standards and protocols, wired and/or wireless networking circuitry (e.g., a communications transceiver).

As known by one skilled in the art, a computing device such as marketplace computing server 110 has one or more memories 116, and each memory comprises any combination of transitory and non-transitory, volatile and non-volatile computer-readable media for reading and writing. Volatile computer-readable media includes, for example, random access memory (RAM). Non-volatile computer-readable media includes, for example, read only memory (ROM), magnetic media such as a hard-disk, an optical disk drive, a flash memory device, a CD-ROM, and/or the like. In some cases, a particular memory is separated virtually or physically into separate areas, such as a first memory, a second memory, a third memory, etc. In these cases, it is understood that the different divisions of memory may be in different devices or embodied in a single memory. Some or all of the stored contents of a memory may include software instructions executable by a processing device to carry out one or more particular acts.

Marketplace computing server 110 further includes operative software found in a conventional computing server such as an operating system, software drivers to direct operations through the I/O circuitry 112, networking circuitry, and other peripheral component circuitry. In addition, marketplace computing server 110 includes operative application software such as network software for communicating with other computing devices, database software for building and maintaining databases, and task management software for distributing the communication and/or operational workload amongst various processing units. In some cases, marketplace computing server 110 is a single hardware machine having the hardware and software listed herein, and in other cases, marketplace computing server 110 is a networked collection of hardware and software machines working together in a server farm to execute the functions of the system to collect personal medical information and provide a computer-based marketplace to sell the collected personal medical information 100. Conventional hardware and software of marketplace computing server 110 is not shown in FIG. 3.

Several other computing devices are also illustrated in FIG. 3 including a laptop computer 110a, a tablet computer 110b, a desktop computer 110c, and a smart phone mobile device 110d. One of skill in the art will recognize that these other computing devices 110a-110d also include components similar to I/O logic 112, processing unit 114, and memory 116, and these components are not illustrated for simplicity.

Memory 116 in FIG. 3 includes a plurality of modules including a database module 118, an information input logic module 122, an information delivery logic 124 module, a Web server/browser logic module 126, an optional (reverse) auction logic module 128, an acceptable buyer terms logic module 130, a buyer modification logic module 132, an acceptable seller terms logic module 134, a seller modification logic module 136, a seller pool logic module 138, a seller compensation logic module 140, an anonymizer logic module 142, and obfuscation logic/de-obfuscation keys logic module 144, and a database searching logic module 146.

Database 118 is a storage module configured as programmatic application to store raw and processed information. Database 118 may be any combination of a traditional database, one or more database systems, a file system, or any other method known in the art for storing such information using known database techniques, including an implementation using distributed computing techniques. Database 118 may include features that permit the database 118 to expand as new information is added and to contract as information is removed. Database 118 includes an interface that permits programmatic database commands and queries, for example, commands and queries generated by information input logic module 122, information delivery logic module 124, and database search logic module 146.

Information stored in database 118 may be stored in records or in some other format. The particular records stored in database 118 can be archived, duplicated, deleted, edited, and the like. In some cases, entire information records or portions of information records may be protected as confidential. For example, obfuscation logic/de-obfuscation keys module 144 may stand alone or cooperate with database 118 to encrypt, obfuscate, or otherwise to store information in a confidential way, and to permit authorized parties to access the information.

Particular information records stored in database 118 may be electronically transferred in whole or in part, and the records may be mined for information, which may then be distributed in return for consideration.

The information input logic module 122 works cooperatively with I/O circuitry 112, database 118, obfuscation logic/de-obfuscation keys module 144, and other modules of the marketplace computing server 110. Information input logic module 122 receives personal medical information produced by an implantable medical device 104 or other personal medical information associated with an individual 102, organizes the personal medical information, and stores the personal medical information in database 118. In some cases, the personal medical information is tagged, obfuscated, aggregated, categorized, modified, or adapted in some other way in association with storage in database 118. The information input logic module 122 also processes external requests to search or retrieve information from database 118. For example, in some cases, information input logic module 122 will receive a request from an outside source for a plurality of productized datasets. The request may define fields that are common to each of the plurality of productized datasets that are sought by a particular source. In the case of medical information, for example, a particular medical device company may seek productized information sets for a particular type of medical device implanted into patients having a particular demographic profile. In this case, the information input logic module 122 will parse the request, and generate one or more queries that are passed to database 118 in search of records that match the defined fields of the request.

The information delivery logic module 124 is configured to customize information into one or more dynamically productizable datasets and deliver productized information sets to an outside source. As discussed herein for personal medical information (as an example, such information may be stored in database 118, and portions of the information may be consolidated and communicated to an outside source. For example, within one embodiment, if a plurality of records are retrieved from database 118, a portion of information in the records may be packaged as part of a sale, lease, license, or other authorized transfer of such information. The information delivery logic module 124 formats the information into one or more sets of productized information. The information delivery logic module 124 also communicates the productized information. In cases where some or all of the information is obfuscated, the information delivery logic module 124 works cooperatively with the obfuscation logic/de-obfuscation keys module 144 to also provide keys or other security information to the outside source such that the productized information is accessible.

The optional (reverse) auction logic module 128 module is arranged to carry out features of a traditional auction or a reverse auction for personal medical information. Generally speaking, traditional auctions are auctions where buyers compete to purchase a good or service, and in contrast, reverse auctions are those auctions where sellers compete for opportunities to provide a good or service. The goal of a traditional auction is to drive up a bidding price, while that of a reverse auction is to drive down the bidding price.

Various parties may want to participate in auctions targeted to the transfer of personal medical information in exchange for consideration based on economic and other incentives. An operator of the marketplace computing server 110 may benefit by charging a fee to provide the auction services. Individuals may benefit by receiving money in exchange for access to their personal medical information. Device makers, medical practitioners, researchers, and others may benefit by having access to a pool of personal medical information that may be searched or customized for their particular use.

When the optional (reverse) auction logic module 128 is set up to conduct a traditional auction, an operator of the marketplace computing server 110 may recognize a need for a particular type of information. For example, information associated with a large number of running shoes as collected from participants in a marathon running race. In this case, if the operator of the marketplace recognizes that access to such information may be valuable to running shoe designers, the operator may form a traditional auction that consolidates such information into a productized dataset and offer access to the information to the highest bidder.

Alternatively, reverse auctions are those auctions where sellers compete to provide their product or service against others that also have a competing product or service to sell. In this case, a large number of individuals 102, 102a-102n may be willing to sell certain personal medical information, for example information associated with particular personal habits. If a buyer is looking for a plurality of such information, there may be more information available than the buyer is looking for. Alternatively, the buyer may be looking for information from a certain percentage of individuals who are willing to provide such information. In the case of a reverse auction, the individuals may provide a price at which they are willing to provide their information. The optional (reverse) auction logic module 128 may be arranged to select productizable datasets from an appropriate number of individuals based on the prices at which the individuals are offering to provide the information.

The acceptable buyer terms logic module 130 works cooperatively with the information input logic module 122 to parse a request for one or more productized datasets. In this case a particular party or entity may wish to buy productized datasets at a particular price, any particular quantity, from a pool of sellers having a particular number of sellers in the pool, according to particular demographics or other qualifying information, any particular price, with respect to a particular date that the information was collected or will be delivered, and according to other conditions. Particularly, the acceptable buyer terms logic module 130 receives and structures terms of a personal medical information transfer that are acceptable to the party that will provide consideration in return for the transfer of the personal medical information.

The buyer modification logic module 132 cooperates with the information input logic module 122 to allow changes to the terms of a personal medical information transaction.

The acceptable seller terms logic module 134 is similar to the acceptable buyer terms logic module 130, and the seller modification logic module 136 is similar to the buyer modification logic module 132. With respect to a particular transaction wherein a plurality of productized datasets are communicated from the marketplace computing server 110 to another computing device 110a-110d associated with a particular buyer, a seller of personal medical information may determine and modify acceptable terms of the transaction.

The seller pool logic module 139 is arranged to manage datasets that have one or more defined fields in common. For example, database 118 may include personal medical information associated with tens, hundreds, thousands, or millions of individuals. A first pool of individuals may include all of the individuals that are biologically male, and a second pool of individuals may include all of the individuals that are biologically female. A third pool of individuals may include all of the individuals that are older than 25 years. It is recognized that the third pool of individuals will in all likelihood include members of both the first and second pools, but members of the first pool are in all likelihood not included as members of the second pool. By way of example above, it is recognized that personal medical information records in database 118 may be parsed and pooled in any number of ways. Seller pool logic module 139 is arranged to identify and retrieve records according to requests that define one or more fields, characteristics, or other criteria.

The seller compensation logic module 140 is configured to recognize when personal medical information associated with a particular individual 102 is included in a productized dataset that is communicated from the marketplace computing server 110 as part of a transaction. In this case, the seller compensation logic module 140 will credit, pay, or otherwise account for compensation (i.e., consideration) on behalf of the particular individual.

Within various embodiments the anonymizer logic module 142 is configured to act on personal medical information during the formation of productized datasets. This may be done for security reasons, government regulation reasons, private contractual reasons, or other reasons. Due to the operations of the anonymizer logic module 142, when an outside party receives productized datasets, the outside party is not able to associate specific portions of personal medical information with any specific individual.

The obfuscation logic/de-obfuscation keys module 144 may be arranged to encrypt, decrypt, or otherwise secure some or all of the personal medical information stored in database 118. The information may be secured to fulfill obligations under contract with individuals that provide personal medical information, obligations under the Health Insurance Portability and Accountability Act (HIPPA), or for some other regulatory, consent, or privacy reason.

The database search logic module 146, as discussed earlier, is arranged to generate, process, or carry out specific inquiries into database 118. The database search logic module 146 may include error correction capabilities, voice recognition, natural language processing for the automatic generation of search inquiries, or other particular features.

Within alternative embodiments of the invention, the database 118 of FIG. 3 may be utilized to store and process a dataset transaction as described in FIG. 1 (e.g., the database 17 of FIG. 1).

A web server/browser logic module 126 includes operative hardware and software to support Internet-style functionality. In some cases, the web server/browser logic module 126 operates as a web server to generate and deliver webpages over network 106 to other computing devices 110a-110d. The generated webpages may include any multimedia type information including audio, video, still images, text, programmatic components executable components interpreted software code, and the like, which may collectively be known by the term, "screen information." In other cases, the web server/browser logic module 126 operates as a web browser to receive webpages and render them on a display device.

As should be readily apparent given the disclosure provided herein, the database 118 (and accompanying software and logic circuits provided in FIGS. 1 and 3) may be composed of a single central unit, or optionally, divided into one or more separate locations. For example, more than one physical database can contain the collective information that is to be processed in a dataset transaction. Similarly, the processing functions can be divided into one or more different physical locations in such a manner so as to still act with one accord.

Figure 4:
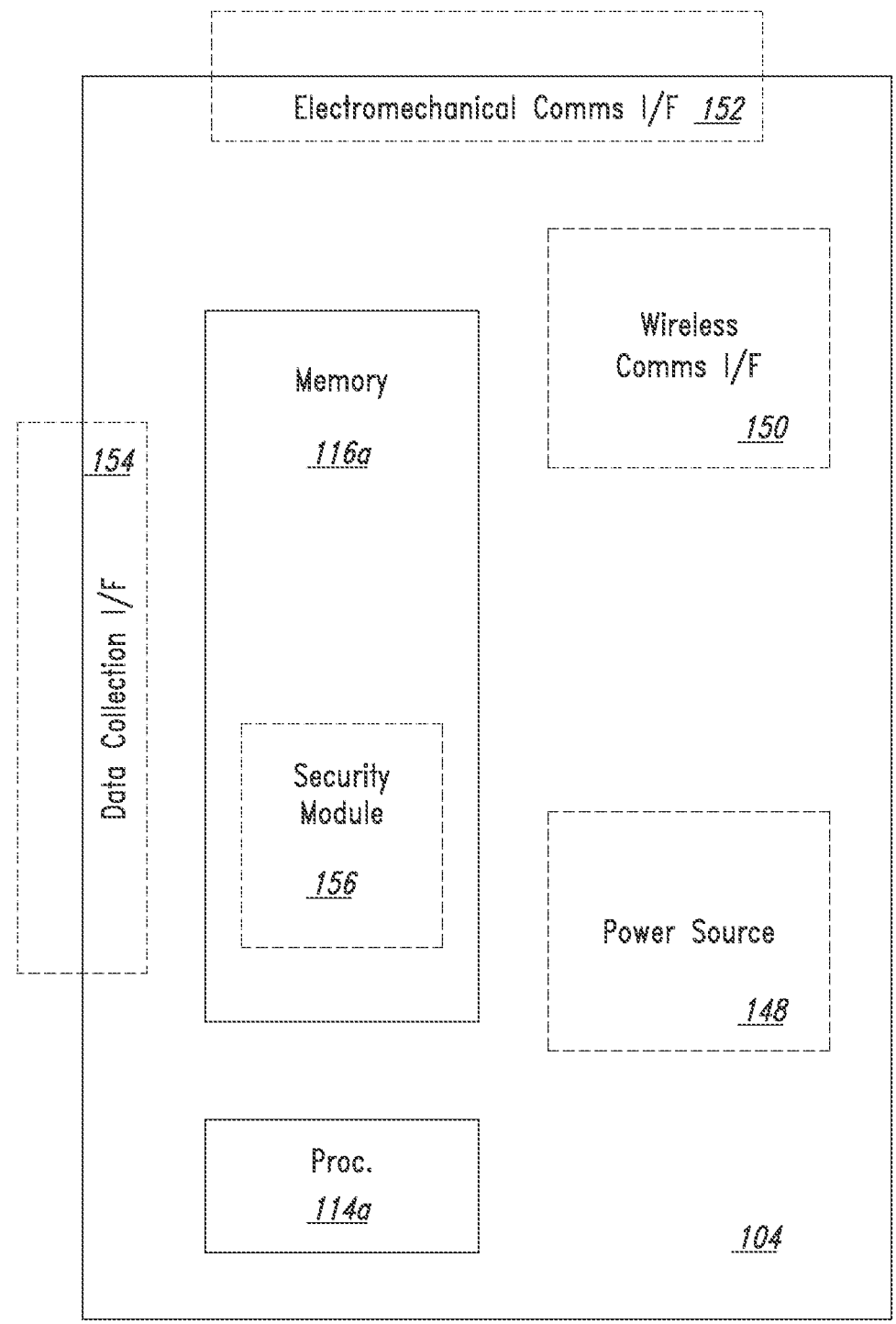
FIG. 4 illustrates one embodiment of an implantable medical device.

FIG. 4 illustrates one representative implantable medical device 104 that includes at least some functional structure 104a. The functional structure 104a will typically define the implantable medical device 104. For example, considering the case when the implantable medical device 104 is an artificial cervical disc, the functional structure 104a may include to cobalt chromium alloy and plates and an ultrahigh molecular weight polyethylene core. As another example, considering the case when the implantable medical device 104 is an artificial hip, the functional structure 104a may include an acetabular cup, a polyethylene insert, a metal femoral head, and a femoral stem.

The implantable medical device 104 includes a processing unit 114a and memory 116a. The processing unit 114a and memory 116a may be particularly suited to an embedded environment. The processing unit 114a and memory 116a have characteristics along the lines of the processing unit 114 and memory 116, respectively, of FIG. 3, though specific details are omitted for brevity.

One or more optional modules may be provided in an implantable medical device 104. For example, the implantable medical device 104 may include a power source 148, a wireless communications interface 150, an electromechanical communications interface 152, an information collection interface 154, and a security module 156. Within one or more embodiments, the information collection interface can collect information from one or more sensors, including for example, fluid pressure sensors, fluid volume sensors, contact sensors, optical sensors, position sensors, pulse pressure sensors, blood volume sensors, blood flow sensors, chemistry sensors (e.g., for blood chemistry and/or other fluids), metabolic sensors (e.g., for blood and/or other fluids), antibodies, accelerometers, mechanical stress sensors and temperature sensors. Within preferred embodiments of the invention, the information collection interface will collect information from multiple sensors, e.g., an accelerometer and a gyroscope, which information is collected and collated along with an internal time stamp.

Power source 148 may include a battery, a capacitor, or circuitry arranged to generate power based on externally provided stimuli. For example, in some cases, power source 148 is a nickel-cadmium battery, a zinc-mercury battery, a lithium-iodine battery, or a battery having some other chemical composition. Such a battery may be rechargeable. In other cases, power source 148 may include an electronic circuit configured to generate power when stimulated by kinetic energy, electromagnetic energy, or some other stimuli. Power generated by power source 148 is passed to processing unit 114a, memory 116a, and optionally other components of the implantable medical device 104.

The optional wireless communication interface 150, when included, is used to communicate information to, from, or to and from the implantable medical device 104. A wireless communication interface 150 may conform to a radio-frequency identification (RFID) protocol, a near field communication (NFC) protocol, and IEEE 802.11 WiFi protocol, or some other protocol. Generally speaking, such protocols permit two or more devices to establish radio communications when the devices are in close physical proximity (e.g., 10 meters or less) to each other. In these cases, the devices operate by electromagnetic induction between two loop antennas; one antenna in the implantable medical device 104 and another antenna in an external communication device. In these cases, the communications may conform to a standardized protocol provided by one or more standardization bodies.

An optional electromechanical communications interface 152, when integrated with an implantable medical device 104, is used to communicate information to, from, or to and from the implantable medical device 104. An implantable medical device 104 may have either or both a wireless communications interface 150 and an electromechanical communications interface 152. The electromechanical communications interface may conform to a standardized protocol provided by one or more standardization bodies, or the electromechanical communications interface 152 may operate according to a proprietary or some other protocol. The electromechanical communications interface 152 may pass information collected by the implantable medical device 104 as a serial bit stream, a parallel set of bits, a sequence of packets, or in some other form.

In some embodiments, the electromechanical communications interface 152 is arranged as a port, housing, cable, or in some other form. In some cases, communications with the implantable medical device 104 occur via a cable plugged in or otherwise communicatively coupled to the electromechanical communications interface 152.

During normal operation, the implantable medical device 104 will collect operational information, fault information, or other types of information. Operational information is generally associated with operation of the functional structure 104a of the implantable medical device 104. For example, operational information may include a count of flexures of an artificial knee or hip joint, a volume of blood passed through a stent, a number of abnormal heart signal detections and corresponding electrical impulse firings of a pacemaker, and the like. Fault information may be any improper, unexpected, or recognized errant information captured by the processing unit 114a, the functional structure 104a, or any other part of the implantable medical device 104. Other types of information may include timing information, temperature information, battery or other power status, or other types of information.

Wireless communications interfaces 150 and electromechanical communication interfaces 152 are controlled by processing unit 114a under direction of software instructions stored in memory 116a. Information collected by the implantable medical device and information targeted toward the implantable medical device 104 may be passed between the wireless communication interface 150 or the electromechanical communications interface 152 and an external communication device such as interface 108 (FIG. 3) or a computing device 110 (FIG. 3). The information may be arranged as a serial bit stream, a sequence of packets, or in some other form.

In addition to information, energy may also be passed through the wireless communication interface 150 or the electromechanical communications interface 152 in cooperation with power source 148. The energy may be used to charge a battery, fill a storage capacitor, power the respective communication interface, power the processing unit 114a, power the memory 116a, and for other reasons.

The optional information collection interface 154 works cooperatively with the functional structure 104a or other parts of the implantable medical device to capture the operational information, fault information, or other types of information. The information collection interface 154 may include electrical components, mechanical components, electromechanical components, or other components. For example, the information collection interface 154 may include electronic timers, temperature sensors, strain gauges, accelerometers, probes, electrodes, moisture sensors, and many other components.

The memory 116a of the implantable medical device 104 may optionally include a security module 156. The security module 156 may be arranged to encrypt information, decrypt information, prevent tampering with software instructions stored in the memory 116a, and the like. In some cases, information that is collected by the implantable medical device 104 is encrypted. The encryption may be performed for compliance with government regulations such as the health insurance portability and accountability act (HIPAA), for security of the information from unauthorized access, or for other reasons. The security module may perform operations according to an advanced encryption standard (AES), a date encryption standard (DES), or some other security protocol.

Figure 5:
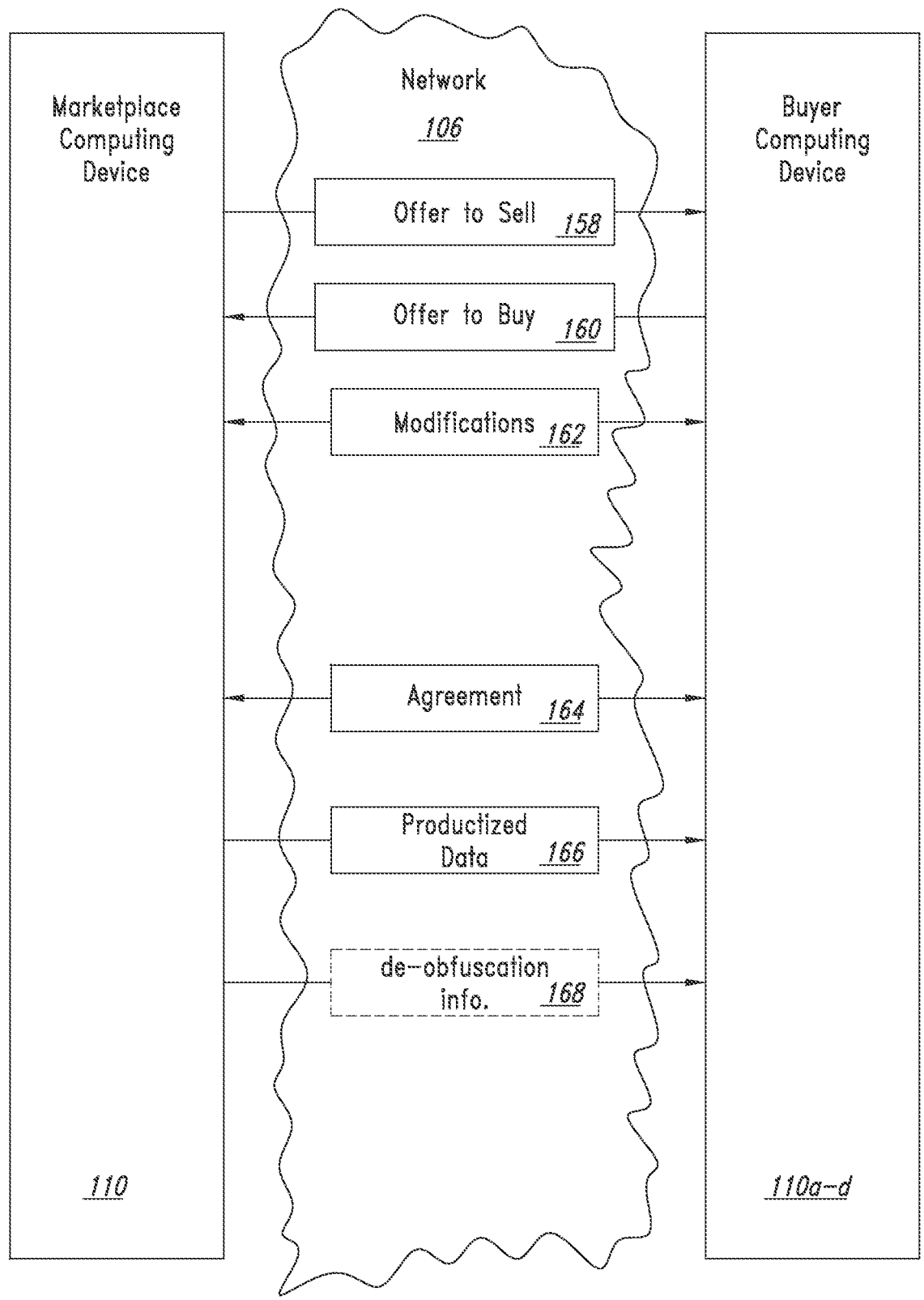
FIG. 5 illustrates one embodiment of an information flow diagram illustrating information communicated between a marketplace computing server and a personal information buyer's computing device.

FIG. 5 is an information flow diagram illustrating information communicated between a marketplace computing server and a personal medical information buyer's computing device. The acts illustrated in the flow diagram may be carried out by a processing unit 114 (FIG. 3) executing software instructions stored in a non-transitory computer-readable storage medium such as memory 116 (FIG. 3).

In FIG. 5, a first marketplace computing device 110 is communicatively coupled through a network 106 to one or more computing devices 110*a-d*, which may be laptop computers, desktop computers, tablet computers, mobile devices, or some other type of computing device. The marketplace computing device 110 maintains a database 118 (FIG. 3), which may be local to marketplace computing device 110 or remotely configured and accessible. In some cases, database 118 is formed as a single information repository in a single location; in other cases, database 118 is formed as two or more information repositories that may reside in one location or in several locations. Some portions or all portions of database 118, marketplace computing device 110, and computing devices 110*a-d* may be distributed across a cloud computing structure facilitated through network 106.

Database 118 is organized as a plurality of records, each of the records having a plurality of fields. Many and in some cases all of the records stored in database 118 are assigned an owner. In many cases, the assigned owner is selected when the record is created as the individual who is the source or subject of the information stored in the record. In other cases, the owner of a record may be re-assigned to a new individual. In some cases, some records do not have on assigned owner.

Alternatively, or in addition, in some cases, one or more curators are granted permission to make decisions regarding a grant of access to the information of a plurality of owners. A particular owner and a particular curator may agree to a set of conditions under which the curator may agree to grant access to the owner's information to a particular buyer. For example, a seller may agree that a curator may agree to transfer certain information to a buyer for a selected price. The permission granted to the curator by an owner of the information may be revocable or irrevocable. The terms under which the permission is granted to the curator may be negotiated between the curator and the particular owner of the information.

Records stored in database 118 may include (as an example), a field for artificial joints. Each field for artificial joints may be associated with other fields (i.e., sub-fields) that specify information about one or more artificial joints implanted in an individual. The specified information may include a date of an associated medical procedure, a type of implanted device, the area of the individual's body with the device has been implanted, manufacturing information such as a model number and serial number of the implanted device, and the hospital and attending physician that performed the procedure. Many other types of information may be stored in fields and records in database 118.

At 158, an offer to sell or otherwise distribute certain information stored in database 118 is presented from marketplace computing device 110 to one or more computing devices 110*a-d*. At 160, an offer to buy or otherwise access certain information stored in database 118 is presented to marketplace computing device 110 from one or more computing devices 110*a-d*. In some cases, both of the offers at 158 and 160 respectively are made, and in other cases, only one of the two offers is made. In some cases, the offer at 158 occurs before the offer at 160, in other cases the offer at 160 occurs before the offer at 158, and in still other cases, both of the offers at 158 and 160 respectively are made concurrently. Generally speaking, in FIG. 5, an offer to distribute information may correspond with a request for access to information, and a request for access to information may correspond with an offer to distribute information.

When the marketplace computing device 110 provides an offer to sell or otherwise distribute certain information at 158, the offer will define particular characteristics of the information being offered. The selected characteristics correspond to information stored in particular fields of records in database 118. For example, an offer to sell may include information selected only from records that owned by individuals who have had a knee replacement using an implanted device provided by a certain medical device manufacturer. In this way, it is understood that an offer to sell certain datasets may identify particular fields within records of the database having common (e.g., identical or substantially the same) information stored in the identified fields.

Correspondingly, an offer to buy information may be received as a request for an information set defining fields common to a plurality of records in database 118.

Prior to providing an offer to sell or otherwise distribute certain information at 158, or after receiving an offer to buy or otherwise access certain information at 160, the marketplace computing device 110 will search or otherwise interrogate records stored in database 118 to determine if the records can satisfy a particular request. Searching database 118 in this way enables the marketplace computing server 110 to find records that contain some or all of the information specified in the particular request (i.e., offer to sell at 158 and offer to buy at 160). When the particular records are found or otherwise identified as matching the defined fields of the request, information from some or all of the records that were found is retrieved. At least some, and in some cases all, of the retrieved information is formed into a plurality of productized datasets.

At 162, the particular offers or requests made at 158 and 160 may be modified. The modification act at 162 may be administered by the marketplace computing server 110, one or more computing devices 110*a-d*, or by a combination of computing devices. The acts at 158, 160, and 162 may be sequential in any order or concurrent. The acts at 158, 160, and 162 may also be iterative such that one or more offers to sell information and one or more offers to buy information are modified two times, three times, or many times.

In some cases, the modifications act at 162 includes a determination of whether an owner of a record will provide information stored in the record in return for consideration. In some cases, the modifications act at 162 includes a seller specifying a price for access to the information, a buyer specifying a price in order to grant access to the information, or both a seller and a buyer specifying a price. The modifications at 162 may include a back and forth negotiation of price or other terms between a seller or individual assigned owner of the information and a buyer that would like access to the information.

In some cases, the acts at 158, 160, and 162 may be organized as an auction. The auction may be directed toward a plurality of buyers of information. In this case, a plurality of buyers may each use a computing device 110*a-d* to enter bids for certain information. The bids may include establishing a price for the information or other terms. Alternatively, the auction may be a reverse auction directed toward a plurality of sellers of information. In this case a buyer may have entered an offer to buy a certain amount of information having certain characteristics defined by fields in the individual records of database 118. If the marketplace computing server 110 is able to access more than enough information to satisfy the request, a reverse auction may be arranged to identify record owners willing to make their information available to the buyer. In this case, sellers may bid against each other by lowering the price at which they are willing to grant access to their information or by agreeing to other terms more favorable to a prospective buyer of the information. This type of reverse auction may be utilized to establish a price or other terms.

In some cases, different owners of the information may agree to different prices or other terms from other owners of information. For example, if a buyer offers to buy ten productized information sets that each has particular characteristics, five owners of information may agree to one price, and five owners of information may agree to another price. In this type of circumstance, a buyer of information may individually negotiate with each seller, or the buyer may simply agree to a set of consolidated terms for access to the information, and the marketplace computing device 110 will manage individual agreed upon terms with individual sellers such that an aggregated dataset will meet the consolidated terms agreed to by the buyer.

Additional functions may also be performed within the modification acts at 162. In some cases, the marketplace computing server 110 is unable to find a sufficient number of records having characteristics that match the characteristics of particular information request. In these cases, the marketplace computing server 110 may search alternative fields or records. As an example, a case is considered wherein a particular request to buy information is received at 160, and the request seeks information from individuals who have had a very specific type of knee replacement surgery. In the case, the request to buy information may narrowly characterize the type of information that is requested by specifying an individual's gender, age range, dates of surgery, replacement knee manufacturer, replacement knee size, replacement knee model number, and many other characteristics. If the marketplace computing server 110 is unable to find a sufficient number of records having the matching characteristics, the marketplace computing server 110 may search multiple genders, a wider age range, different dates of surgery, different replacement knee model numbers, and the like. The marketplace computing server 110 will then present information about the alternative fields or records thereby providing a prospective buyer an opportunity to agree to such alternative information or otherwise modify a request for information. As particular offers are being modified, the marketplace computing device 110 may facilitate communications with individual owners of information to determine if the individual owners are willing to provide their information for an agreed-upon consideration.

Other functions that may be performed within the modification acts at 162 include seeking information from one or more alternative databases, soliciting new information from current owners of information that have assigned records within database 118, and seeking information from new owners that do not currently have any assigned records within database 118.

At 164, agreement is reached. Agreement indicates that the marketplace computing server 110 has identified a sufficient number of records that contain information having the characteristics that interest a particular buyer, and the terms of a transfer of the information have been agreed to. The terms are sufficiently defined such that the marketplace computing server 110 clearly identify and deliver the agreed-upon information at an agreed-upon time and in an agreed-upon manner, and the computing device 110a-d can receive the agreed-upon information at the agreed-upon time and in the agreed-upon manner. In addition, the computing device 100a-d can deliver the agreed-upon consideration at an agreed-upon time and in an agreed-upon manner, and the marketplace computing server 110 can receive the same.

Without limitation, agreement functions at 164 include the programmatic mechanisms to establish, confirm, maintain, and verify, price information, timing information, quantity information, security information, licensing or other qualified use of information, and the like. Table 1 sets forth a list of a non-limiting, exemplary terms of agreement. The agreement functions at 164 may include all of the terms in Table 1, some of the terms in Table 1, or different terms than those identified in Table 1.

TABLE 1

Non-limiting, Exemplary Terms of Agreement

Price (Per Record, Per Information Set, Per Month, etc.)
Number of Records (Fixed, Variable, etc.)
Delivery Date(s)
Optional Security Information (De-Obfuscation, etc.)
Information Terms of Use At 166, the marketplace computing server 110 productizes the identified records retrieved from database 118 and delivers the productized information to the computing device 110a-d. Productizing the information includes formatting the retrieved records in an agreed-upon manner. For example, in some cases, the records are formatted into a single productized dataset such as a spreadsheet. In other cases, one or more records are formatted into a plurality of productized datasets. A dataset may take the form of a spreadsheet, an extensible markup language (XML) document, a human readable text document, a portable document format (PDF) document, a stream of digital information bits, a set of information printed on paper, one or more information files stored on a memory device, or in some other form.

In some cases, certain information such as personal information identifying a specific record owner is removed or otherwise not captured. In some cases, certain information such as information identifying a specific record owner is obfuscated such as by encryption. Other information may also be left out or obfuscated in a productized dataset. In some cases, the information that is left out or obfuscated from a productized dataset is based on the agreed-upon terms between a buyer and seller.

At 168, optional acts may be performed to transfer de-obfuscation information from the marketplace computing server 110 to a computing device 110a-d. The de-obfuscation information may include, for example, security keys that permit a known decryption algorithm to decrypt or otherwise restore obfuscated productized information.

Figure 6:
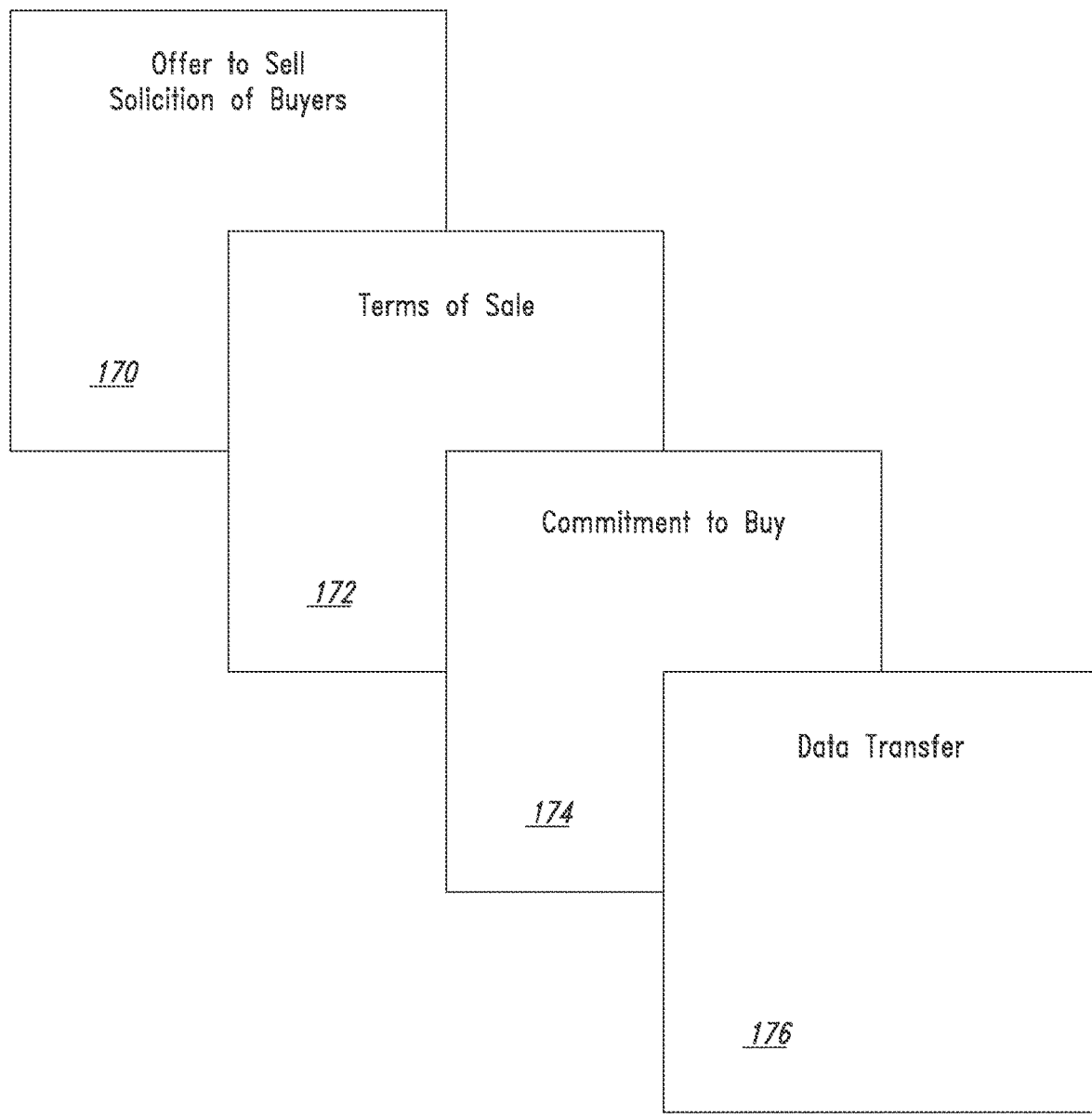
FIG. 6 illustrates one embodiment of an implementation of screen information communicated via the computer-based marketplace.

FIG. 6 is an implementation of screen information communicated via the computer-based marketplace. The screen information communicated in FIG. 6 may be associated with the information flow diagram of FIG. 5. In this way, a computer-based marketplace implemented via a marketplace computing server 110 may include web server functionality arranged to host a website. The website is accessible via computing devices 110a-d through network 106.

The website hosted by the marketplace computing server 110 is arranged to serve a plurality of interactive web pages.

Four exemplary web pages are illustrated in FIG. 6 as first, second, third, and fourth sets of screen information 170-176, respectively.

The first set of screen information 170 may include one or more webpages directed to an offer to sell information, a solicitation of buyers to purchase information, a request to purchase information, or some other set of screen information that facilitates the transfer of productized information sets. The first set of screen information 170 may be associated with acts 158, 160, 162 in FIG. 5.

The second set of screen information 172 may include one or more web pages directed to terms of sale associated with one or more productized information sets. The second set of screen information 172 may be associated with acts 158, 160, 162, and 164 in FIG. 5.

The third set of screen information 174 may include one or more web pages directed to a commitment to buy one or more productized datasets. The third set of screen information 174 may be associated with acts 162 and 164 in FIG. 5.

The fourth set of screen information 176 may include one or more web pages directed to the transfer of one or more productized datasets from the marketplace computing server 110 to a computing device 100a-d. The fourth set of screen information 176 may be associated with acts 166 and 168 and FIG. 5.

FIG. 7 is a representative embodiment of acceptable seller terms and acceptable buyer terms for a personal medical information transaction. The personal medical information transaction may be carried out according to the information flow illustrated in FIG. 5 and in conjunction with a website delivering screen information as illustrated in FIG. 6.

In the particular personal medical information transaction, a computer-based marketplace maintains a database 118 formed of a plurality of records, each record associated with an individual owner. The respective individual owners may have previously expressed an interest in selling information associated with a particular medical condition.

FIG. 7 illustrates a particular record of one seller wherein individual fields in the record represent personal information (e.g., personal medical information) exclusive to the respective seller. That is, personal information stored in the record is associated with the specific individual. For example, if the record identifies a particular date of medical treatment, the date represents the day that the specific individual was medically treated. As another example, if the record identifies a particular medical practitioner that performed a procedure, the identified medical practitioner performed the procedure on the owner of the record. Any other information may be similarly personal to an individual owner or subject of a database record. Accordingly, when information in a record is associated with, exclusive to, or in some other way linked to a particular seller, owner, patient, or the like, the information is understood to indicate an action, occurrence, description, person, place, or thing experienced by the particular individual.

The record may include a particular Record ID used to distinguish the record from other records in database 118. The record may also include personal information such as a name, address, date of birth, and gender. Such personally identifying information may be removed or obfuscated when information from the particular record is formulated in a productized dataset.

Other fields in the personal information seller record are associated with one or more particular medical devices. Generally speaking, each medical device may be an implanted medical device 104 (FIG. 3), and the associated information may include the type of device, the manufacturer, a model number, a serial number, a location in the body where the device is implanted, a date that medical device was implanted, one or more dates of re-operation, any complications of the original implant surgery or re-operation, notes from medical personnel, communication capabilities of the device, some or all of the information retrieved from the medical device, software version information, battery information, a fault or other error information, representative information associated with use of the medical device (e.g., number of repetitions, load, stress, and the like), patient-reported information (pain, function, activity, quality of life, sleep, medication usage, emotional and psychological wellbeing, and rehabilitation efforts) associated with the medical device or procedure, and any other information. In some cases, particular fields are accessible and left open so that other information may be added to the field in Association with a particular medical device.

Still other fields in the personal information seller record are associated with personal habits of a record owner, physical traits of a record owner, and still other information. In some cases, a personal information seller record, or a different type of database record associated with the personal information seller record indicates certain terms of sale. For example, in FIG. 7, fields indicate a particular set of prices that an exemplary seller is willing to accept in exchange for access to certain information. In one field, for example (i.e., Price D+F+G), a price is entered that the particular seller is willing to accept for access to date of birth information and information associated with a first medical device. In another field, for example (i.e., Price D+E+L+M), a price is entered that the particular seller is willing to accept for access to date of birth information, gender information, and information associated with a different medical device. In this way, each individual record owner may prospectively set out particular acceptable terms (e.g., price, timing, and the like) for the transfer of an associated set of information.

FIG. 7 also illustrates another exemplary record associated with a particular buyer. Some or all of the fields in the exemplary record associated with the particular buyer may correspond to fields associated with a record of a particular seller. For example, the record may include a particular Record ID used to distinguish the record from other records in database 118. The record may also include personal information such as an address, a date of birth, and a gender, along with other information regarding one or more particular implantable medical devices, personal habits, physical traits, and other such information. These fields represent characteristics of the type of information that the particular personal information buyer is seeking. The fields are used by the marketplace computing server 110 (FIG. 5) two search database 118 (FIG. 5).

In some cases, a personal information buyer record, or a different type of database record associated with the personal information buyer record indicates certain terms of an offer to purchase productized information. For example, in FIG. 7, fields indicate a particular set of prices that an exemplary buyer is offering in order to receive access to certain information. In one field, for example (i.e., Price D+F+G), a price is entered that the particular buyer is offering for access to date of birth information and information associated with a first medical device. In this case, the marketplace computing server 110 is able to easily determine if the exemplary seller and exemplary buyer agree on the terms of a particular sale.

In correspondence with the devices and information flow operations of FIGS. 5 and 6, it is understood that particular fields of particular records in database 118 may be dynamically modified as various buyers and sellers negotiate terms for the transfer of information.

Figure 8A:
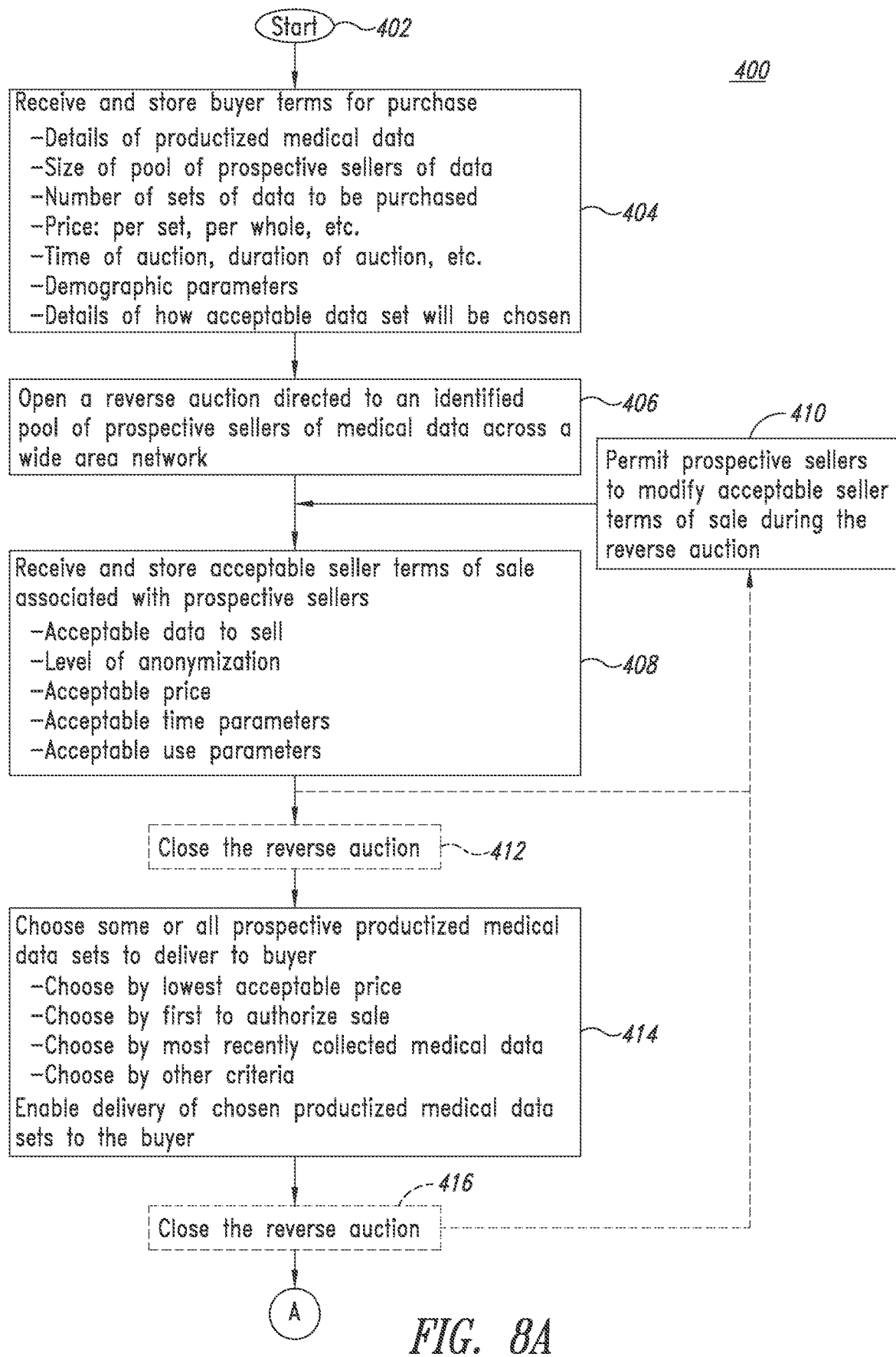
FIGS. 8A and 8B are a flow diagrams representing one example of a personal information transaction.
Figure 8B:
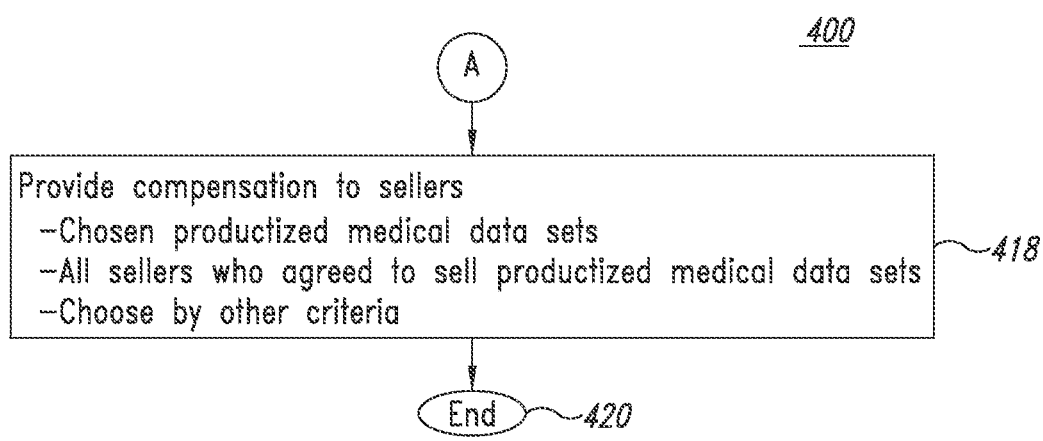

FIGS. 8A and 8B are a flow diagram representing a personal medical information transaction 400. The personal medical information transaction is represented as a plurality of modules which include computing hardware and software as represented in other figures and described in other text of the present disclosure. In FIGS. 8A and 8B, the particular transaction is represented as a reverse auction wherein a particular buyer sets up terms for a purchase of personal medical information. One or more owners or curators of personal medical information are made aware of the reverse auction, and the one or more owners or curators are permitted to agree to the buyer's terms or counter-offer with a particular set of prospective seller terms.

Processing in FIG. 8A Begins at 402.

At 404 a computer-based marketplace receives and stores a particular set of buyer terms for a purchase of productized medical information. In the particular example, the buyer terms for purchase may include a size of a pool of prospective sellers and a number of sets of information to be purchased. In this way, a buyer may receive assurance that a sufficient quantity of information exists from which to draw a representative sample having a predetermined size. The buyer terms may also include a price for each particular productized dataset, a price for a whole quantity of information, or a price defined according to some other term.

In some cases, the prospective buyer of the information may set up terms for the reverse auction including when the auction will begin, how long the auction will be open, and win the auction will close. Buyer terms may also include demographic parameters to define particular characteristics of prospective sellers of information, geographic parameters to define location details associated with prospective sellers, and other parameters that define characteristics of acceptable medical datasets.

At 406 a reverse auction is opened and directed to an identified pool of prospective sellers of medical information. The prospective sellers of medical information may be the individual owners of medical information or curators of a plurality of particular datasets. The reverse auction is administered by the marketplace computing server 110 (FIG. 5) and conducted across a network. The network may be a wide area network (WAN) such as the Internet, a local area network (LAN), or some other network, and the reverse auction may be carried out via one or more web pages of a website.

At 408, a plurality of acceptable terms of sale associated with one or more prospective sellers of personal medical information are received. The prospective sellers, or curators of such medical information, may enter such terms as the particular information that will be sold or otherwise transferred, whether and how personally identifying information will be removed or obfuscated, the acceptable uses of their medical information, the acceptable buyers of their information, and when the information will be delivered. The prospective seller terms may also include terms of permissive use for the information such as a time period during which the information may be used, the type of medical study or research that the information may be used in, and other terms of use. The prospective seller terms may also include an acceptable price at which the prospective seller is willing to sell or otherwise transfer and permit use of the personal medical information.

In some cases, the reverse auction will close at 412. In these cases, the auction may close because time has expired. Alternatively, the auction may close because the buyer and seller terms are in agreement. If the auction closes, processing falls to 414; alternatively, processing advances to 410.

At 410, if the auction remains open, the prospective sellers of personal medical information may modify their acceptable terms of sale. In many cases, the modification is a reduction in price at which the prospective sellers are willing to accept. For example, if a buyer of personal medical information is offering to buy certain personal medical information from 500 individuals at a particular price, and if there are more than 500 prospective sellers of information that matches the buyer's parameters, then at least some of the prospective sellers may reduce the price they are willing to accept in order to have their information included. Many prospective sellers of information would rather accept a lower price in order to earn some money than hold out for a higher price at the risk of earning no money. Processing at 410 advances back to processing at 408 where the marketplace computing server 110 receives and stores the updated set of acceptable seller terms.

At 414, the information that will be delivered to the buyer is selected from the pool of prospective sellers. Returning to the example of the buyer of personal medical information offering to buy information from 500 individuals, the reverse auction may draw more than 500 prospective sellers. If there is an available pool of more information than the buyer is offering to buy, then only some of the prospective sellers will have their information sold. The specific records that are selected from which to draw the information that is sold may be chosen based on a lowest acceptable price, the order in which authorizations for the sale are received, the most or least recently collected information, a random selection, or by some other criteria.

After the information to be sold is selected, the information will be productized and prepared for delivery to the buyer. In some cases, such as when only some of the information desired by the buyer is available or otherwise selected, the reverse auction will remain open and processing will return to 410. In these cases, prospective sellers may be able to further modify their acceptable terms of sale.

Alternatively, the reverse auction will close at 416, and processing will pass to 418.

At 418, compensation will be distributed to the owner's or seller of the personal medical information. The compensation is provided to those owners or sellers of the chosen personal medical information that has been productized into one or more medical information sets and delivered to the buyer.

Processing in the personal medical information transaction 400 of FIGS. 8A and 8B ends at 420.

C. One Representative Example of an Artificial Joint

Figure 9A:
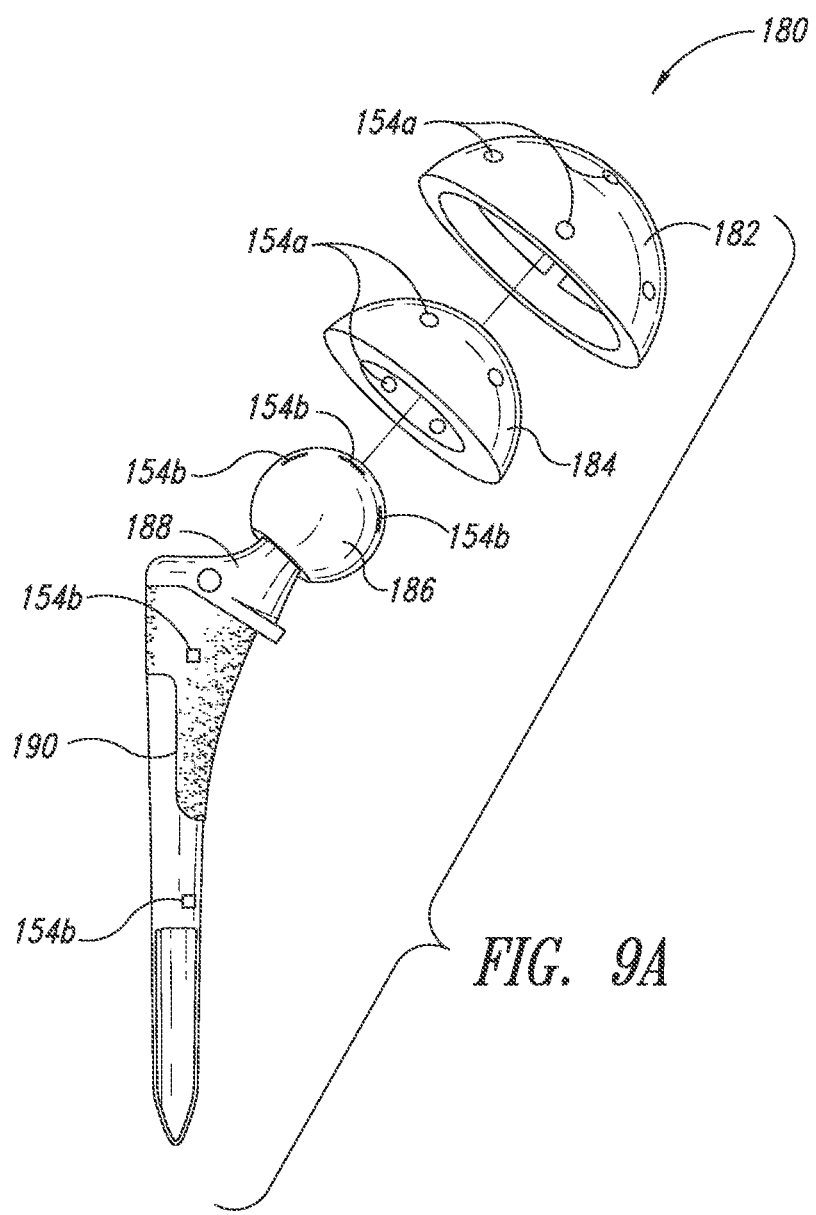
FIG. 9A illustrates one embodiment of an artificial hip joint in exploded view.

FIG. 9A is an exploded perspective view of artificial hip joint embodiment 180. In many cases, individuals facing osteoarthritis in one or both of their hips are candidates for hip replacement surgery, also called hip arthroplasty. In hip arthroplasty, the acetabulum of the pelvis and femoral head of the upper thighbone are replaced by a medical practitioner with a device such as the artificial hip joint embodiment 180 of FIG. 9A.

The artificial hip joint embodiment 180 includes an acetabular cup 182, a polyethylene insert 184, a femoral head 186, a neck 188, and a femoral stem 190. The embodiment 180 may include one or more information collection interface modules, e.g., two different modules such as illustrated by modules 154a and 154b. The information collection interface modules may include strain gauges, accelerometers, repetition counters, step counters, motion detectors, position sensors, migration detectors, vibration sensors, temperature sensors, and many other types of detection devices. During the surgical procedure, the femoral head of individual's upper thighbone (i.e., the femur) is removed (e.g., sawed off), and the individual's acetabulum is reamed or otherwise formed into the shape of a half-sphere. The half-sphere formed in the individual's acetabulum is sized to mate perfectly with the outer surface of the acetabular cup 182. In some cases, the acetabular cup 182 is cemented to the bone of the individual; in other cases, the acetabular cup 182 has a porous surface to which the individual's bone will attach during healing. Correspondingly, the femoral stem 190 is pressed into the interior space (marrow cavity) of the individual's femur, which is exposed when the femoral head of the upper thighbone is removed. Like the acetabular cup 182, in some cases, the femoral stem 190 is cemented in place, and in other cases the femoral stem 190 has a porous surface to allow bonding with the bone during healing.

After the acetabular cup 182 and femoral stem 190 are placed, the medical practitioner will assemble the pieces of the artificial hip joint. As illustrated in FIG. 9A, the neck 188 of the artificial hip is coupled to the femoral head 186, and the femoral head will rotationally fit within in the polyethylene insert 184. The thick muscles of the buttock and thigh provide sufficient pressure and bias to keep femoral head 186 securely located within the hollow partial sphere of the polyethylene insert 184.

It has been learned that artificial hip surgeries are generally safe and provide tangible benefits to individuals. On the other hand, it has also been learned that not every artificial hip medical procedure is completely successful. For example, just like a real hip, an artificial hip can dislocate if the ball (i.e., femoral head 186) comes out of the socket (i.e., polyethylene insert 184). As other examples, parts of the artificial hip 180 or the patient's bone structure can wear out, cement used to secure the acetabular cup 182 or the femoral stem 190 can break down allowing parts to loosen, parts of the artificial joint can be overstressed and break, and other complications can also arise. In order to address these and other complications with conventional artificial hips, technology-enabled artificial joints have been developed.

Figure 9B:
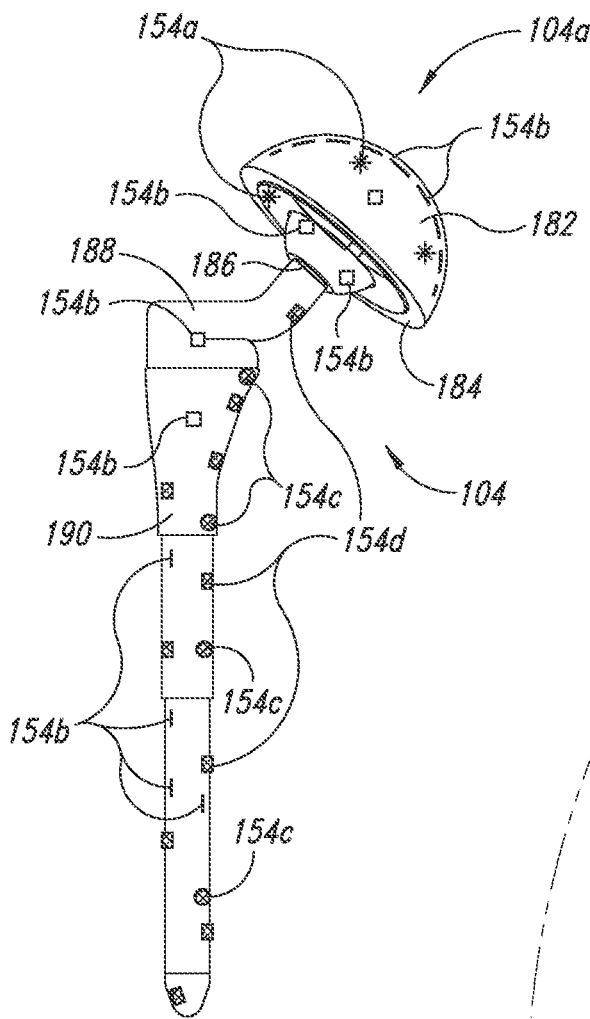
FIG. 9B illustrates one embodiment of an implantable artificial hip joint having a plurality of sensors.

FIG. 9B is an implantable medical device artificial hip joint embodiment 104. The implantable medical device artificial hip joint embodiment of FIG. 9B may correspond to the implantable medical device 104 of FIG. 3. In addition, it is recognized that the artificial hip embodiment 180 of FIG. 9A forms the basis of the functional structure 104a of the implantable medical device 104. The functional structure 104a includes the acetabular cup 182, the polyethylene insert 184, the femoral head 186, the neck 188, and the femoral stem 190.

The functional structure 104a also includes various information collection interface modules. A first information collection interface module 154a includes a strain gauge physically coupled to the surface of the acetabular cup 182. The strain gauge forms one leg of a Wheatstone bridge electronic circuit configuration that includes a power source and a signal detection device V. As the acetabular cup 182 is subject to various physical stress forces, deflection in the strain gauge is represented in the signal detection device V. The amplitude of the detected signal can generally be translated into a measurement of force in one or more directions placed on the acetabular cup 182.

The functional structure 104a also includes additional information collection interface modules 154b, 154c, and 154d. More or fewer such modules may also be arranged in contact or proximity with the functional structure 104a. The information collection interface modules may include strain gauges, accelerometers, step counters, repetition counters, motion detectors, position sensors, vibration sensors, temperature sensors, migration detectors, and many other types of detection devices. The information collection interface modules may be based on micro-electromechanical systems (MEMS), electronic devices, mechanical devices, electromechanical devices, or other types of sensing technologies.

With respect to the artificial hip embodiment, one or more information collection interface modules 154a-d may be used to generate or otherwise collect information associated with the operation of the artificial hip, and the operations to generate or otherwise collect the information may be autonomous or facilitated via processor 114a. The information associated with the information collection interface modules may be stored in memory 116a.

As described in the present disclosure, information collected within the implantable medical device 104 may be communicated via a network 106 or interface 108 to a marketplace computing server device 110. The information may further be stored as described herein in one or more database records or fields and formed into one or more productized data sets.

Figure 9C:
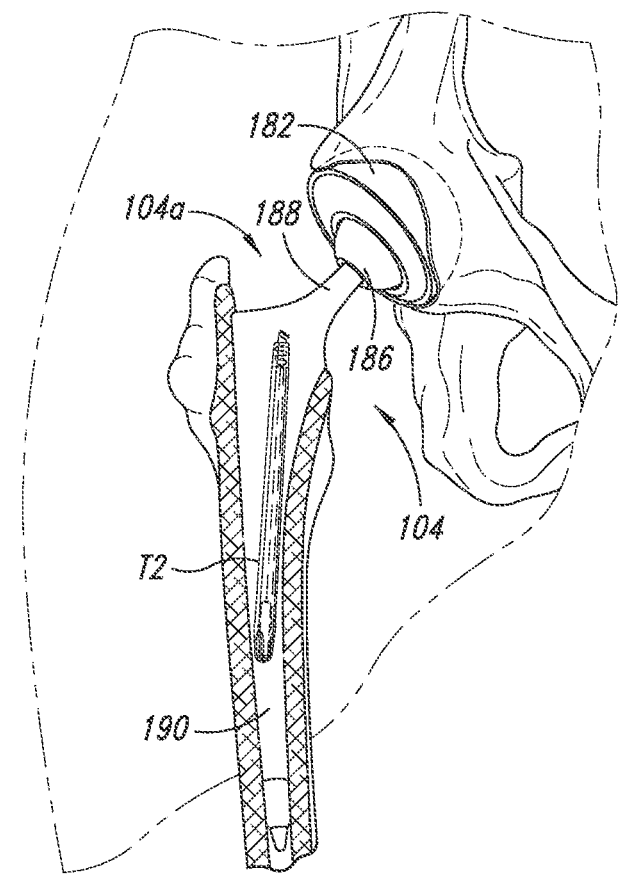
FIG. 9C illustrates one embodiment of an implanted implantable artificial hip joint having a sensor module therein.

FIG. 9C shows an implanted implantable medical device artificial hip joint embodiment 104. The implanted medical device artificial hip joint embodiment of FIG. 9C may correspond to the implanted implantable medical device 104 of FIG. 3. In addition, it is recognized that the artificial hip embodiment 180 of FIG. 9A forms the basis of the functional structure 104a of the implantable medical device 104. The functional structure 104a includes the acetabular cup 182, the polyethylene insert 184 (not shown), the femoral head 186, the neck 188, and the femoral stem 190. The functional structure 104a also includes one or more information collection interface modules, e.g., the module referred to as T2. Within this embodiment T2 may comprise a variety of sensors (e.g., strain gauges, accelerometers, gyroscopes, repetition counters, step counters, motion detectors, position sensors, vibration sensors, migration detectors, temperature sensors, and many other types of detection devices. Within preferred aspects of this embodiment, the sensor module T2, is placed as shown in the tibial extension of the artificial hip implant. The implantable sensor module can have a battery to power the unit, as well as other components which are helpful and/or necessary to transfer collected information to outside of the body (e.g., various controllers as provided herein, a suitable antennae, and the like).

D. General Considerations

The computer-based marketplace for personal medical information system discussed herein may be configured as a plurality of modules. As used herein, the term "module" refers to an electronic circuit, a processor (e.g., distributed, shared, dedicated, group, single core, multicore, or the like) and memory operative to execute one or more software or firmware programs, an application specific integrated circuit (ASIC), a combinational-logic circuit, or some other individual or cooperative coupling of suitable components (either hardware or software) that provide the functionality described with respect to the module.

As further described herein, a module may include software instructions that are executed by a computing server or a personal computing device. A computing server and a personal computing device includes operative hardware found in conventional computing apparatuses such as one or more central processing units (CPUs), volatile and nonvolatile memory, serial and parallel input/output (I/O) circuitry compliant with various standards and protocols, wired and/or wireless networking circuitry (e.g., a communications transceiver).

As known by one skilled in the art, computing servers and personal computing devices have one or more memories, each memory comprising any combination of volatile and nonvolatile computer-readable media for reading and writing. Volatile computer-readable media include, for example, random access memory (RAM). Nonvolatile computer-readable media include, for example, read-only memory (ROM), magnetic media such as a hard disk, an optical disk drive, a flash memory device, a CD-ROM, and in addition or in the alternative, other information storage devices. In some cases, a particular memory is separated virtually or physically into separate areas, such as a first memory, a second memory, a third memory, etc. In these cases, it is understood that the different divisions of memory may be in different devices or embodied in a single memory.

Computing servers and personal computing devices further include operative software found in conventional computing devices such as an operating system, software drivers to direct operations through the I/O circuitry, networking circuitry, and other peripheral component circuitry. In addition, computing servers and personal computing devices include operative application software such as network software for communicating with other computing devices, database software for building and maintaining databases, and task-management software for distributing the communication and operational workload amongst various CPUs. In some cases, a computing device is a single hardware machine having the hardware and software described herein, and in other cases, a computing device is a networked collection of hardware and software machines working together (e.g., in a server farm) to execute the functions of the computer-based marketplace for personal medical information system.

In the foregoing description, certain specific details are set forth to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks have not been shown or described in detail to avoid unnecessarily obscuring descriptions of the embodiments.

Unless the context requires otherwise, throughout the specification and claims that follow, the word "comprise" and variations thereof, such as, "comprises" and "comprising" are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content and context clearly dictates otherwise. It should also be noted that the conjunctive terms, "and" and "or" are generally employed in the broadest sense to include "and/or" unless the content and context clearly dictates inclusivity or exclusivity as the case may be. In addition, the composition of "and" and "or" when recited herein as "and/or" is intended to encompass an embodiment that includes all of the associated items or ideas and one or more other alternative embodiments that include fewer than all of the associated items or ideas.

The headings and Abstract of the Disclosure provided herein are for convenience only and do not interpret the scope or meaning of the embodiments.

The various embodiments described herein can be combined to provide further embodiments. Aspects of the embodiments can be modified, if necessary, to employ concepts of the various patents, application, and publications to provide yet further embodiments. These and other changes can be made to the embodiments in light of the above-detailed description. Exemplary embodiments of the present disclosure include the following:

1) A non-transitory computer-readable storage medium whose stored contents configure a computing system to perform a method, the method comprising:
   a. maintaining at least one database having information stored therein, said database being organized as a plurality of records, wherein each of said records has a plurality of fields, and wherein each record is owned by an owner, at least some of the information being exclusive to each respective owner;
   b. receiving a request for a dataset, the request defining fields common to said records;
   c. determining if said records can satisfy the request by:
      i. searching said database to find records that contain some or all of the information specified in the request; and
      ii. retrieving information from at least some of the found records that match the defined fields of the request; and
   d. forming at least some of the retrieved information into a plurality of productized datasets.

Within various embodiments of the above the dataset request may be provided by one or more third parties. Within further embodiments, the one or more third-parties may, for example: i) be retained to provide the dataset request; ii) may offer to provide a dataset request; and/or iii) be compensated to provide the dataset request (either before or after successful completion of the request);

2) The non-transitory computer-readable storage medium according to embodiment 1 whose stored contents configure the computing system to perform the method, the method further comprising: e. determining if an owner of a record will provide their retrieved information for consideration. Within other embodiments the method further comprises the step of determining whether there is a consideration match between a buyer or buyers and a seller or sellers. Within related embodiments information is matched in a manner illustrated by the subroutine provided in FIG. 2A.

3) The non-transitory computer-readable storage medium according to embodiments 1 or 2 whose stored contents configure the computing system to perform the method, wherein each of a buyer and a seller specify a price. Within various embodiments consideration is matched in a manner illustrated by the subroutine provided in FIG. 2B.

4) The non-transitory computer-readable storage medium according to embodiments 1 or 2 whose stored contents configure the computing system to perform the method, wherein an auction is utilized to establish a price.

Within various embodiments an auction pool is evaluated in a manner illustrated by the subroutine provided in FIG. 2C. Within yet other embodiments auctions can be executed in a manner illustrated by the subroutine provided in FIG. 2D.

5) The non-transitory computer-readable storage medium according to embodiment 1 whose stored contents configure the computing system to perform the method, the method further comprising:
   a. determining whether alternative fields or records will satisfy the request.
6) The non-transitory computer-readable storage medium according to embodiment 5 whose stored contents configure the computing system to perform the method, the method further comprising:
   a. determining if an owner of a first record will provide their retrieved information for consideration.
7) The non-transitory computer-readable storage medium according to embodiments 5 or 6 whose stored contents configure the computing system to perform the method, wherein each of a buyer and a seller specify a price.
8) The non-transitory computer-readable storage medium according to embodiments 5 or 6 whose stored contents configure the computing system to perform the method, wherein an auction is utilized to establish a price.
9) The non-transitory computer-readable storage medium according to embodiment 1 whose stored contents configure the computing system to perform the method, the method further comprising:
   a. seeking information from an alternative database.
10) The non-transitory computer-readable storage medium according to embodiment 1 whose stored contents configure the computing system to perform the method, the method further comprising:
    a. soliciting new information from current owners.
11) The non-transitory computer-readable storage medium according to embodiment 1 whose stored contents configure the computing system to perform the method, the method further comprising:
    a. seeking information from new owners.
12) The non-transitory computer-readable storage medium according to any one of embodiments 1 to 11 wherein said information is personal information.
13) The non-transitory computer-readable storage medium according to any one of embodiments 1 to 11 wherein said information can be any of a number of forms of information, including for example, information obtained from usage of social media, internet and other sites (e.g., Facebook, Twitter, Reddit, Instagram, Snapchat, WhatsApp, Tumblr, and so on), search engines (e.g., Google, Bing, Yahoo!, etc.), and credit bureaus (including for example, financial and insurance records. Other examples of information include driving records, credit score, search engine history, purchasing behavior, marital and familial status, travel, purchases and so on.
14) The non-transitory computer-readable storage medium according to any one of embodiments 1 to 11 wherein said information is personal medical information. Representative examples of personal medical can be obtained from a large number of sources such as physician and hospital visits, diagnostic procedures, medical and surgical procedures, laboratory tests, imaging studies, superficial monitoring devices, implanted medical devices, physiological testing, psychological testing, rehabilitation procedures, genomic information, subjective information (patient reported symptoms and experiences), and health and fitness monitoring.
15) The non-transitory computer-readable storage medium according to any one of embodiments 1 to 11 wherein said information is obtained from an external (e.g., a wearable device). Representative examples of wearable devices include for example, FitBits, Garmin GPS and tracking devices, (e.g., wearable items, sports equipment, an area of play, and/or external medical devices) having one or more sensors as provided herein include those described in the following patent applications (all of which are hereby incorporated by reference in their entirety): U.S. Ser. No. 62/220,239 and U.S. Ser. No. 15/268,575 entitled DEVICES, SYSTEMS AND METHODS FOR USING AND MONITORING SPORTS EQUIPMENT AND SPORTS ACTIVITIES, as well as U.S. Pat. Nos. 8,180,591 and 8,475,367, and U.S. Serial Nos. 2014/0275852, 2014/0142403, US2014/0197946, US2014/0180019, US2014/0164611, US2014/0135612 and US2015/0182797. Other examples of external devices include, for example, those described in U.S. Pat. No. 5,363,842, and in U.S. Serial Nos. 2009/0194104, 2010/016860 and 2010/019294, 2013/0317379, 2014/0316296, and 2015/0126889.
16) The non-transitory computer-readable storage medium according to any one of embodiments 1 to 11 wherein said information is obtained from an implanted medical device. Within representative embodiments the device is one of those described in the following patent applications, which are hereby incorporated by reference in their entirety: U.S. Ser. No. 14/654,529 and International Application No. PCT/US2013/077356, entitled STENT GRAFT MONITORING ASSEMBLY AND METHOD OF USE THEREOF; U.S. Ser. No. 14/776,646 and International Application No. PCT/US2014/028323, entitled STENT MONITORING ASSEMBLY AND METHOD OF USE THEREOF; U.S. Ser. No. 14/776,650 and International Application No. PCT/US2014/028381, entitled DEVICES, SYSTEMS AND METHODS FOR MONITORING HIP REPLACEMENTS; U.S. Ser. No. 14/392,173 and International Application No. PCT/US2014/043736, entitled DEVICES, SYSTEMS AND METHODS FOR MONITORING KNEE REPLACEMENTS; U.S. Ser. No. 15/320,275 and International Application No. PCT/US2015/037823, entitled DEVICES, SYSTEMS AND METHODS FOR USING AND MONITORING TUBES IN BODY PASSAGEWAYS; U.S. Ser. No. 15/320,279 and International Application No. PCT/US2015/037803, entitled DEVICES, SYSTEMS AND METHODS FOR USING AND MONITORING IMPLANTS; U.S. Ser. No. 15/320,284 and International Application No. PCT/US2015/037825, entitled DEVICES, SYSTEMS AND METHODS FOR USING AND MONITORING SPINAL IMPLANTS; U.S. Ser. No. 15/320,289 and International Application No. PCT/US2015/037827, entitled DEVICES, SYSTEMS AND METHODS FOR USING AND MONITORING ORTHOPEDIC HARDWARE; U.S. Ser. No. 15/320,292 and International Application No. PCT/US2015/0037828, entitled POLYMERS, SYSTEMS AND METHODS FOR USING AND MONITORING POLYMERS FOR USE IN MEDICAL POLYMERS, IMPLANTS, AND PROCEDURES; U.S. Ser. No. 15/320,296 and International Application No. PCT/

US2015/037810, entitled DEVICES, SYSTEMS AND METHODS FOR USING AND MONITORING HEART VALVES; U.S. Ser. No. 15/078,604 and International Application No. PCT/US2015/050789, entitled DEVICES, SYSTEMS AND METHODS FOR USING AND MONITORING MEDICAL DEVICES; and U.S. Serial Nos. 62/312,072, 62/312,079, 62/312,095, 62/312,108, 62/312,114, 62/312,120, 62/312,131, 62/312,180, 62/312,188, 62/312,193, 62/312,197, and 62/312,205.

17) The non-transitory computer-readable storage medium according to any one of embodiments 1 to 11 wherein said information is obtained from an implanted wireless sensor module. Within various embodiments, the sensor module can have at least one of a fluid pressure sensor, fluid volume sensor, contact sensor, position sensor, pulse pressure sensor, blood volume sensor, blood flow sensor, chemistry sensor, metabolic sensor, accelerometer, mechanical stress sensor and temperature sensor. Within further embodiments the sensor module can have (in addition to one or more sensors such as an accelerometer, gyroscope, pressure sensor and the like), one or more of a sensor interface, a processor interface, battery and battery management, and a wireless interface.

18) The non-transitory computer-readable storage medium according to any one of embodiments 1 to 17 wherein said request for a dataset is made by a patient, a physician, a hospital, a company (e.g., a medical device or pharmaceutical company), an insurance company, a healthcare payer, a researcher, a government, governmental entity, or non-governmental entity, a public health policy maker, a consumer products company, purchasers of advertising of any type, providers of services of many types, including, but not limited to, legal, accounting, rehabilitation, renovation, travel-related services, automotive companies, and so on.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system comprising:
a plurality of wearable devices each configured to be worn by a respective owner and each comprising a sensor configured to measure one or more properties representing a status, function or physiology of the respective owner and to generate information corresponding to the one or more properties; and
a computing server having one or more processors, a memory, and a communications transceiver, and a non-transitory computer-readable storage medium whose stored contents configure the computing server to perform a method comprising:
   a) obtaining, through the communications transceiver, information from the plurality of wearable devices corresponding to the one or more properties;
   b) maintaining, in the memory, at least one database having stored therein, at least a portion of the information obtained from the plurality of wearable devices, said database being organized as a plurality of records, each record associated with a respective owner and having a plurality of fields including at least one field having associated therewith information obtained from a wearable device worn by the respective owner;
   c) receiving, through the communications transceiver, a request comprising: i) a specification for a dataset identifying one or more fields, specified information associated with the one or more identified fields, and a specified quantity of records to be included in the dataset, wherein the specified information comprises a type of wearable device, and at least one type of the one or more properties measurable by the sensor, and ii) a specification for consideration specifying a compensation to be provided to the respective owner of the information;
   d) determining, by the one or more processors, if one or more records satisfy the request by: i) searching said database to find records that contain some or all of the specified information and that satisfy the specification for consideration; and ii) retrieving information from at least some of the found records;
   e) wherein determining if one or more records satisfy the request further comprises: presenting information on discrepancy between the specification for consideration and the compensation included in the plurality of records in the auction pool; and
   f) forming, by the one or more processors, a productized dataset comprising at least some of the retrieved information.

2. The system of claim 1, wherein the stored contents of the non-transitory computer-readable storage medium configure the computing server to perform the method, the method further comprising repeating the determining until at least the specified quantity of records is found.

3. The system of claim 2, wherein the stored contents of the non-transitory computer-readable storage medium configure the computing server to perform the method, wherein determining if one or more records satisfy the request further comprises, responsive to a failure to find the specified quantity of records: modifying the specification for a dataset without modifying the specification for consideration; and repeating the determining until the specified quantity of records is found.

4. The system of claim 3, wherein the stored contents of the non-transitory computer-readable storage medium configure the computing server to perform the method, the method further comprising: presenting information on the records found based on the modified specification for a dataset; and receiving a notice of acceptance of the records found based on the modified specification for a dataset.

5. The system of claim 2, wherein the stored contents of the non-transitory computer-readable storage medium configure the computing server to perform the method, wherein determining if one or more records satisfy the request further comprises, responsive to a failure to find the specified quantity of records: soliciting a modification of the specification for a dataset; and repeating the determining based on the modified specification for a dataset until the specified quantity of records is found.

6. The system of claim 2, wherein the stored contents of the non-transitory computer-readable storage medium configure the computing server to perform the method, wherein determining if one or more records satisfy the request further comprises, responsive to a failure to find the specified quantity of records: soliciting a modification of the specification for consideration; and repeating the determining based on the modified specification for consideration until the specified quantity of records is found.

7. The system of claim 2, wherein the stored contents of the non-transitory computer-readable storage medium configure the computing server to perform the method, wherein determining if one or more records satisfy the request further comprises, responsive to a record that does not satisfy the specification for a dataset: soliciting a modification of the record to include new information that results in the record satisfying the specification for a dataset; receiving the modification of the record; and repeating the determining with respect to the modified record.

8. The system of claim 2, wherein the stored contents of the non-transitory computer-readable storage medium configure the computing server to perform the method, wherein determining if one or more records satisfy the request further comprises: identifying a plurality of records that satisfies the specification for a dataset but not the specification for consideration; and adding the plurality of records to an auction pool.

9. The system of claim 8, wherein the stored contents of the non-transitory computer-readable storage medium configure the computing server to perform the method, wherein determining if one or more records satisfy the request further comprises: receiving a modification of one or more of the plurality of records in the auction pool to include a new compensation that results in the one or more records satisfying the specification for consideration.

10. The system of claim 2, wherein the stored contents of the non-transitory computer-readable storage configure the computing server to perform the method, wherein responsive to the quantity of found records being greater than the specified quantity of records, the method further comprising: soliciting a modification of one or more found records to include a new compensation less than the original compensation that results in the one or more records satisfying a revised specification for consideration.

11. The system of claim 1, wherein the specification for consideration further comprises one or more terms of use for the information in the dataset.

12. The system of claim 1, wherein the stored contents of the non-transitory computer-readable storage medium configure the computing server to perform the method, wherein forming a productized dataset comprising at least some of the retrieved information comprises one or more of removing personally identifiable information from the retrieved information, obfuscating the retrieved information, preparing and/or implementing a terms-of use for the retrieved information, and forming the retrieved information into one or more computer-readable files.

13. The system of claim 1, wherein the sensor comprises one of a fluid pressure sensor, fluid volume sensor, contact sensor, position sensor, pulse pressure sensor, blood volume sensor, blood flow sensor, chemistry sensor, metabolic sensor, accelerometer, mechanical stress sensor, temperature sensor, mechanical pressure sensor, gyroscope, strain gauges, auditory sensor, optical system and/or sensor, time sensor.

14. The system of claim 1, wherein the one or more properties measurable by the sensor include one or more of a measure of flexures, pressure, force, load, stress, steps, repetitive movements, motion, position, vibration, temperature, migration, heart rate, blood pressure, temperature, and glucose level.

15. The system of claim 1, wherein the plurality of wearable devices are implantable medical devices, each configured to be implanted in a respective owner and each comprising a functional structure having the sensor, wherein the sensor is configured to measure one or more physical properties and to generate information corresponding to the one or more physical properties.

16. The system of claim 15, wherein the one or more physical properties measurable by the sensor include one or more of a measure of flexures, pressure, force, load, stress, steps, repetitive movements, motion, position, vibration, migration, acceleration, velocity, location.

17. The system of claim 15, wherein the implantable medical device is an artificial joint.

18. The system of claim 17, wherein the artificial joint is a hip prothesis and the functional structure comprises one of an acetabular cup, a polyethylene insert, a femoral head, a neck, and a femoral stem.

* * * * *